(12) United States Patent
Ichise

(10) Patent No.: US 8,652,440 B2
(45) Date of Patent: Feb. 18, 2014

(54) METHODS FOR DIAGNOSING DISEASES AND EVALUATING TREATMENTS THEREFOR USING PET

(75) Inventor: Masanori Ichise, Scarsdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 667 days.

(21) Appl. No.: 12/451,305

(22) PCT Filed: May 9, 2008

(86) PCT No.: PCT/US2008/005994
§ 371 (c)(1),
(2), (4) Date: Mar. 22, 2010

(87) PCT Pub. No.: WO2008/140779
PCT Pub. Date: Nov. 20, 2008

(65) Prior Publication Data
US 2010/0196274 A1     Aug. 5, 2010

Related U.S. Application Data

(60) Provisional application No. 60/928,738, filed on May 10, 2007, provisional application No. 60/937,622, filed on Jun. 28, 2007.

(51) Int. Cl.
*A61K 51/00*     (2006.01)
*A61M 36/14*     (2006.01)

(52) U.S. Cl.
USPC ........................ 424/1.81; 424/1.11; 424/9.1

(58) Field of Classification Search
None
See application file for complete search history.

(56) References Cited

U.S. PATENT DOCUMENTS

| 5,278,308 A | 1/1994 | Kung |
| 5,762,937 A | 6/1998 | Atkinson et al. |
| 2003/0009098 A1 * | 1/2003 | Jack et al. ................. 600/410 |
| 2003/0236391 A1 * | 12/2003 | Klunk et al. ................. 534/11 |
| 2005/0260697 A1 | 11/2005 | Wang et al. |
| 2006/0117397 A1 | 6/2006 | Rutkowski et al. |

OTHER PUBLICATIONS

Souza et al. J. Clin. INvest. 116:1506-1513 (2006).*
Klunk et al. J. Neurosci. 25(46):10598-10606 (2005).*
Carson, et al. "Muscarinic cholinergic receptor measurements with [18F]FP-TZTP: Control and Competition Studies" J. Cereb Blood Flow Metab 18:1130-42 (1998).
Carson, et al. "Kinetic analysis of the muscarinic Cholinergic Ligand [F-18] FP-TZTP in Humans" J Nucl Med 40:30P (1999).
Cohen, et al. "Higher in vivo Muscarinic-2 Receptor Distribution Volumes in Aging Subjects With an . . . " Synapse 49:150-156 (2003).
Ichise, et al. "Linearized Reference Tissue Parametric Imaging Methods: Application to [11C]DASB Positron . . . " J. Cereb Blood Flow Metab., 23:1096-1112 (2003).

* cited by examiner

*Primary Examiner* — Michael G Hartley
*Assistant Examiner* — Sean R Donohue
(74) *Attorney, Agent, or Firm* — Bryan Cave LLP

(57) ABSTRACT

The present invention relates to methods for determining whether a mammal has a disease, such as diabetes, using PET data analysis techniques. These methods include administering to a mammal a PET-compatible tracer, such as a radioligand specific for a vesicular monoamine transporter 2 (VMAT2) receptor, and measuring total functional β-cell capacity (volume) of the mammal's pancreas using PET data analysis techniques. Methods for tracking the efficacy of a treatment for diabetes, for evaluating the regeneration of β-cells in a pancreas, and for monitoring a patient with a transplanted pancreas are also provided.

7 Claims, 25 Drawing Sheets
(16 of 25 Drawing Sheet(s) Filed in Color)

FIG. 3
3A
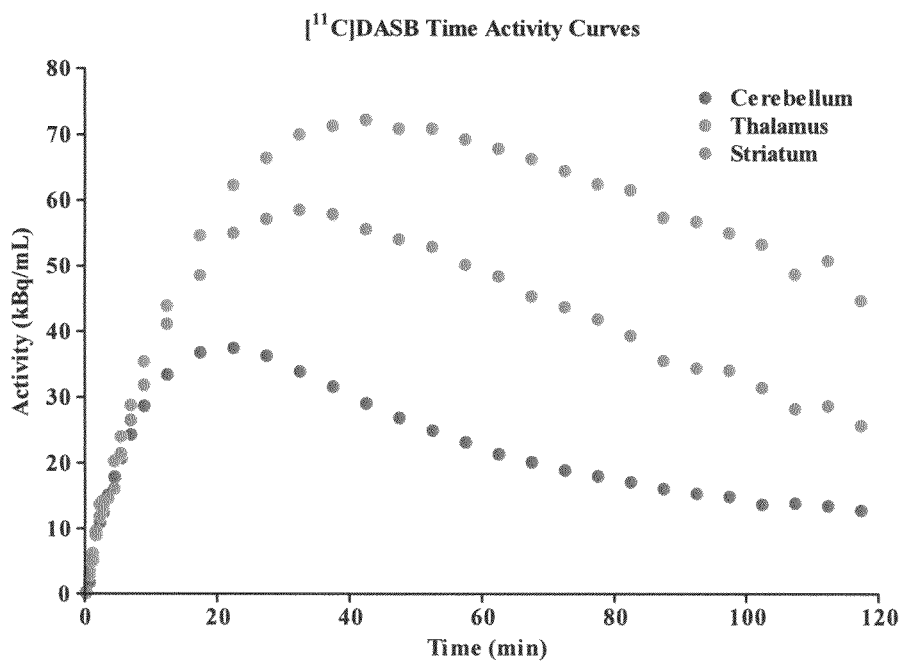
3B
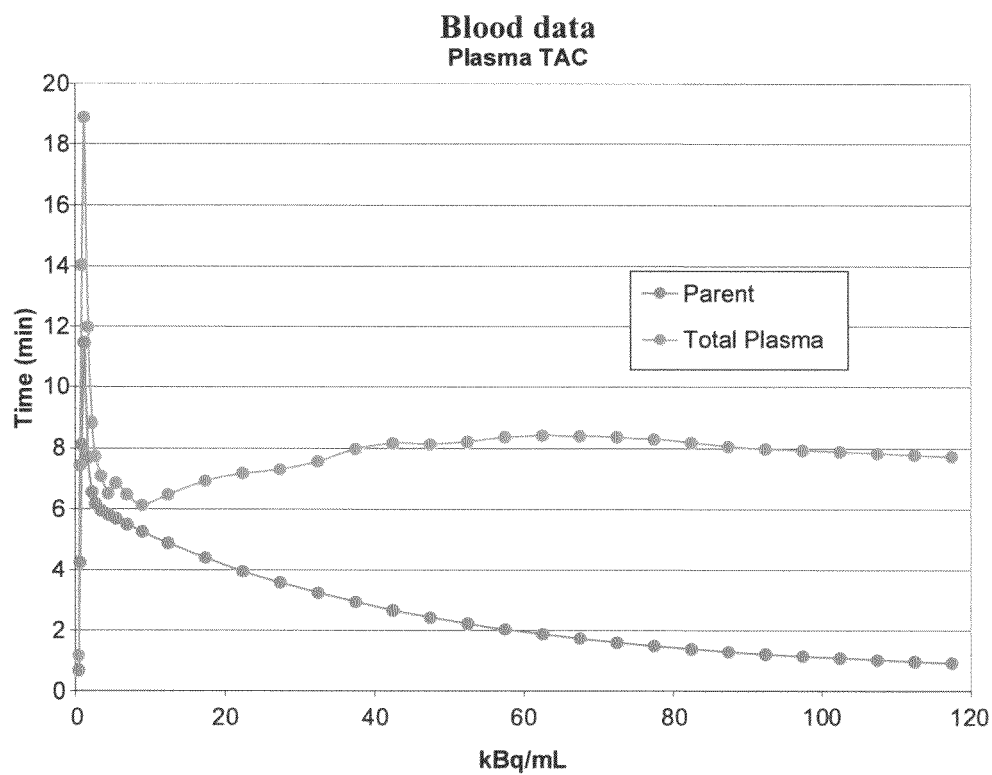

FIG. 5
5A  MRI for volume and map of organs
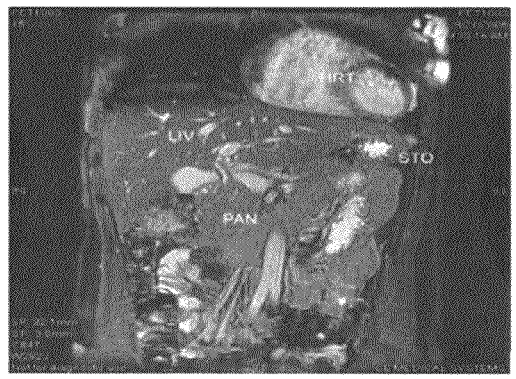
5B  Not much VMAT2 in surrounding tissue
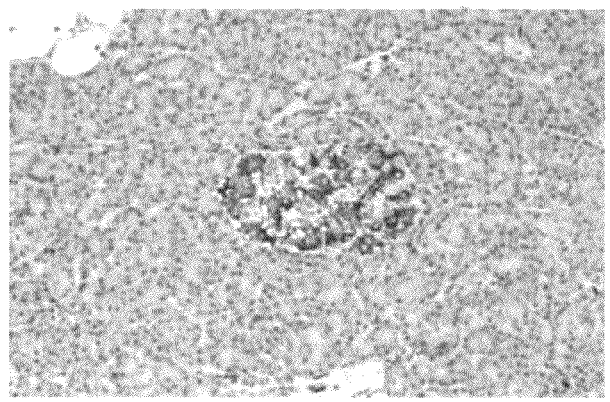
5C
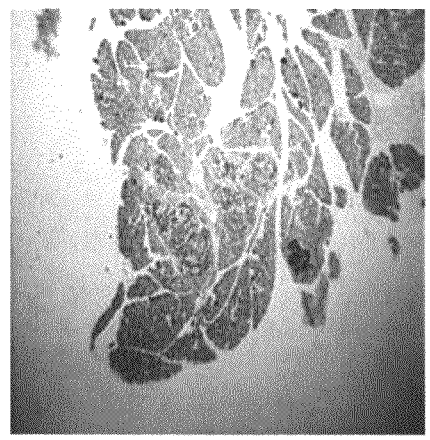

FIG. 7
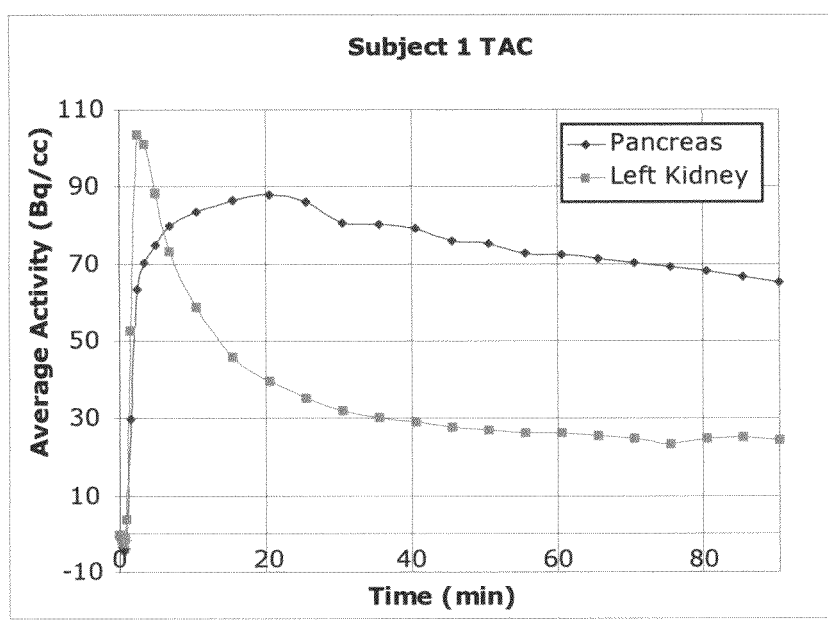
7A
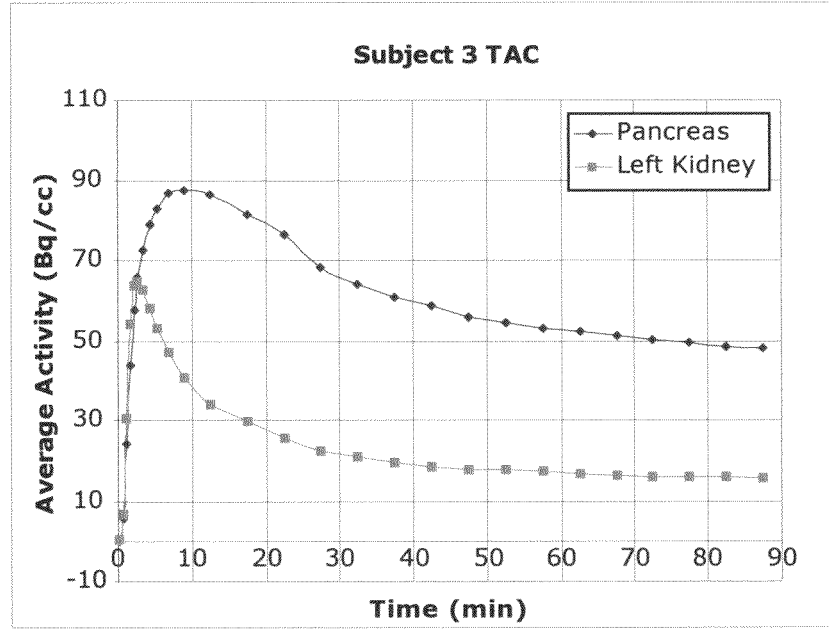
7B

FIG. 9
Non-fitting BP map     Sum 0-30 min
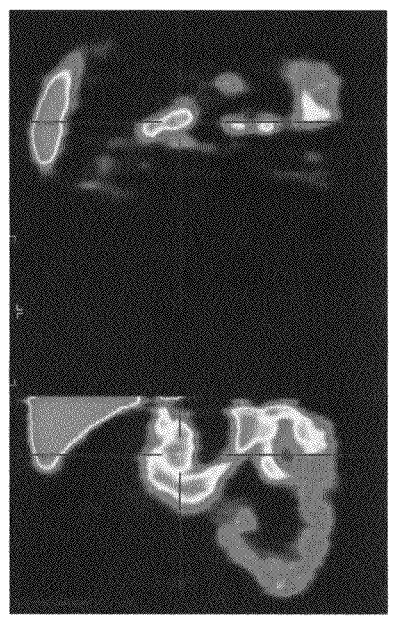
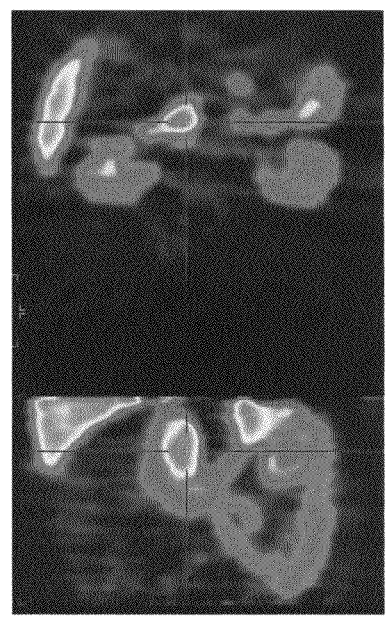
9A                     9B FIG. 10
$$C(T) = -\frac{V}{V'b}\left(\int_0^T C'(t)dt + \frac{1}{k_2'}C'(T)\right) + \frac{1}{b}\int_0^T C(t)dt$$
10A
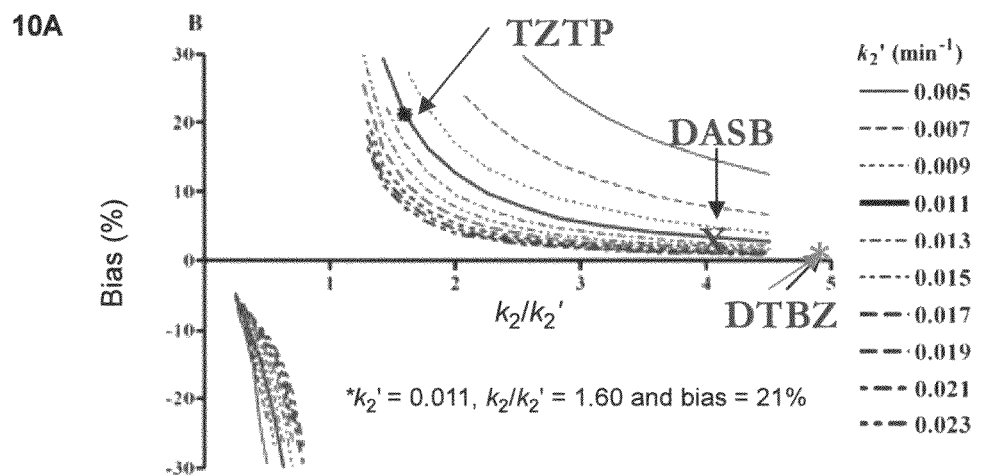
10B
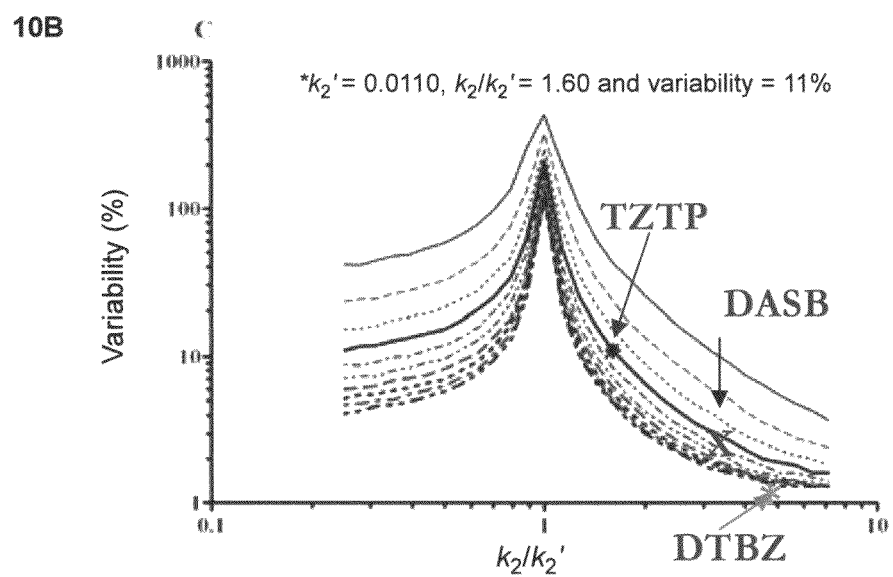

FIG. 11
11A - MRTM2 BP
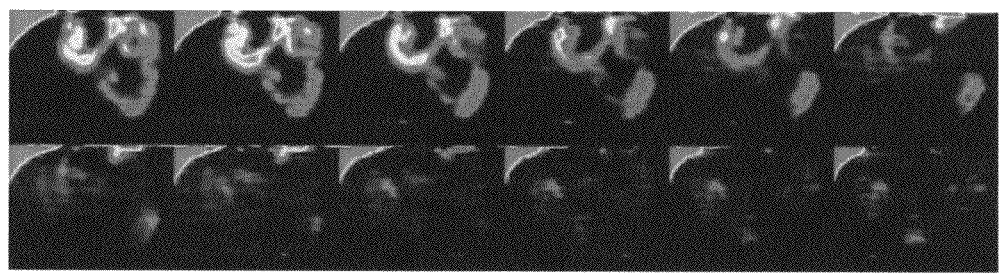
11B - MRTM2 $R_1$
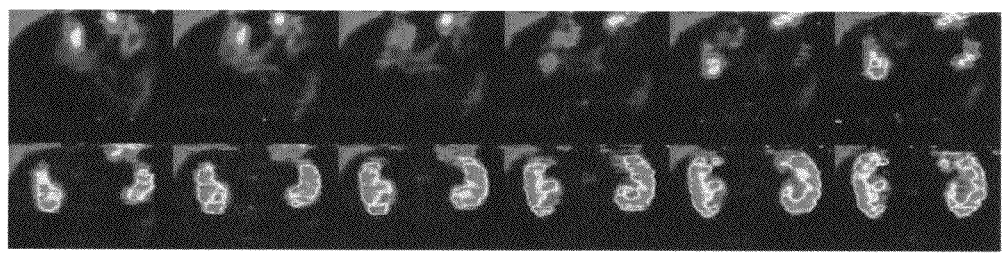

FIG. 15
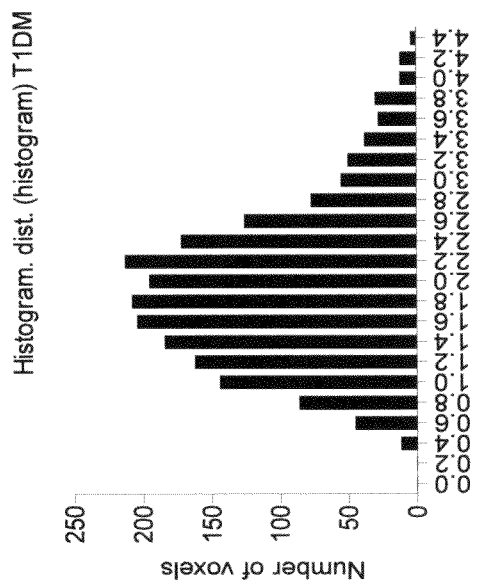
15A
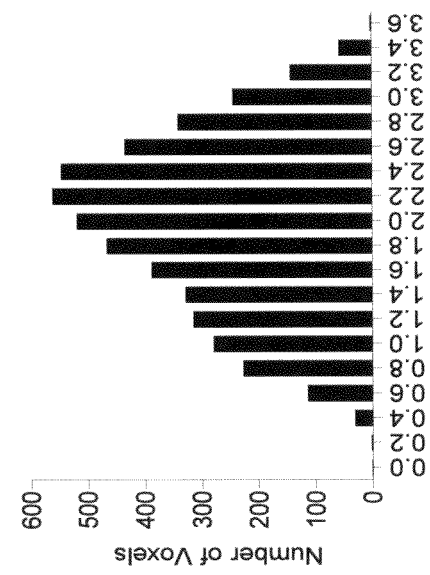
15B
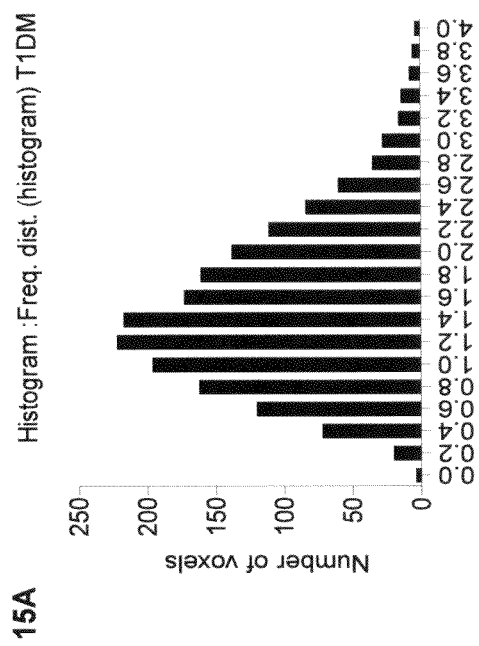
15C
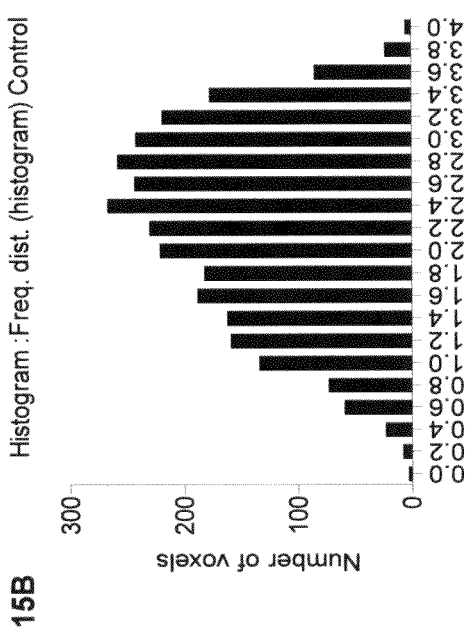
15D

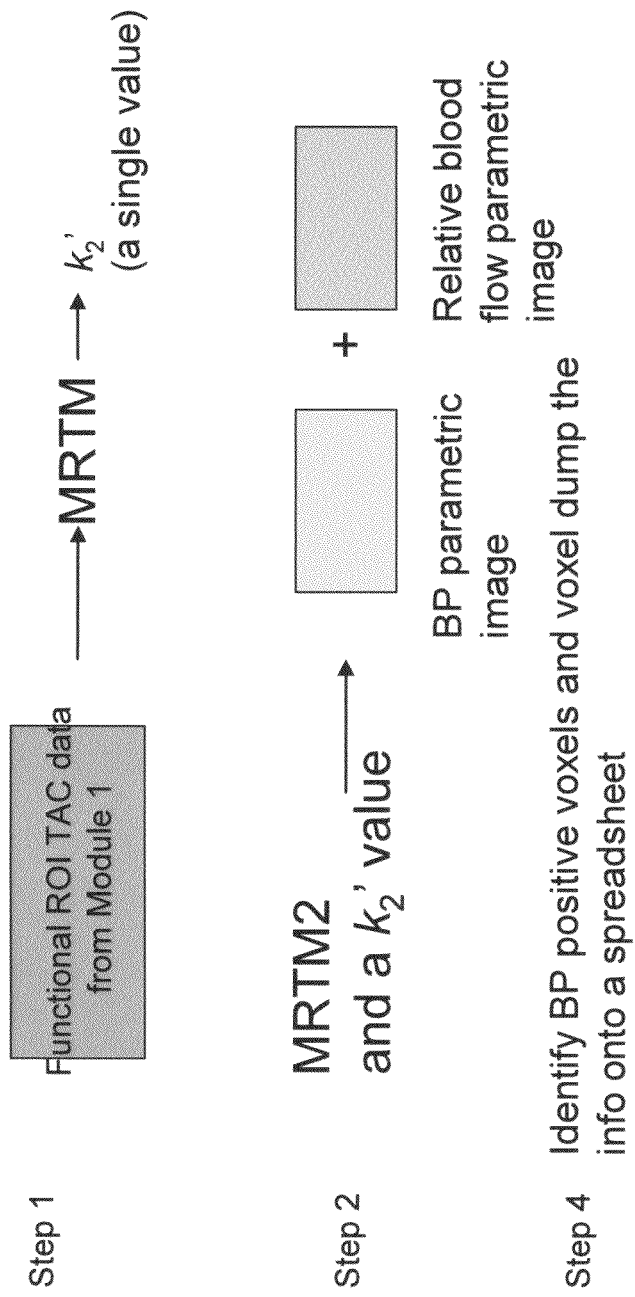

FIG. 22

PANC MAP: Diagnostic Tool for Quantification of Significant Binding Capacity of β-cell Mass of Pancreas (Module 3)

*Profiling of voxel VMAT 2 BP and determination of Significant Binding Capacity (SBC)*

Step 1    Identify BP positive voxels and voxel dump the info onto a spreadsheet-From Module 2 (Module 1)

Step 2    Generation of frequency distribution plot of BP

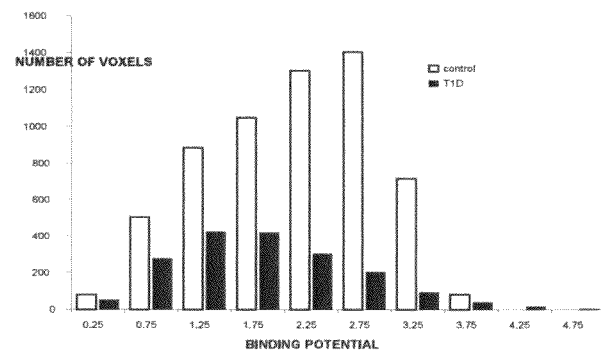

Step 3    Calculation of SBC and comparison of patients and controls
Significant Binding Capacity (SBC) = β (individual voxel *BP* above predetermined significant value x voxel volume

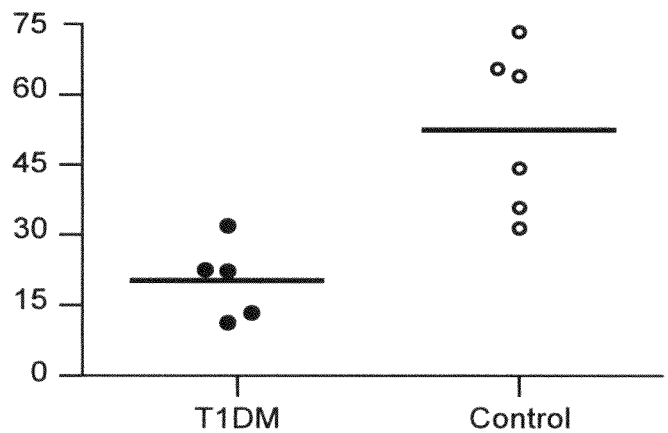

FIG. 25
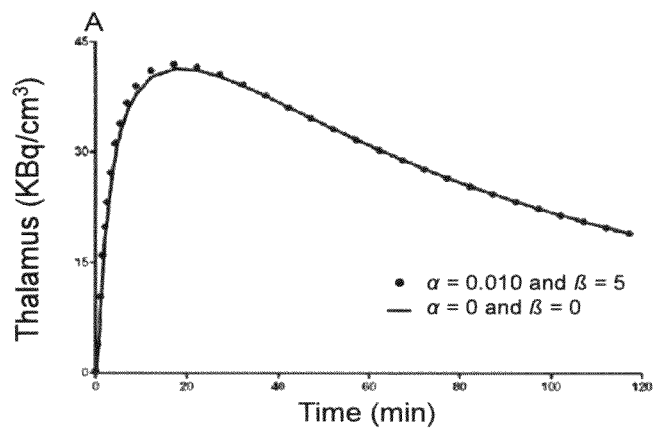
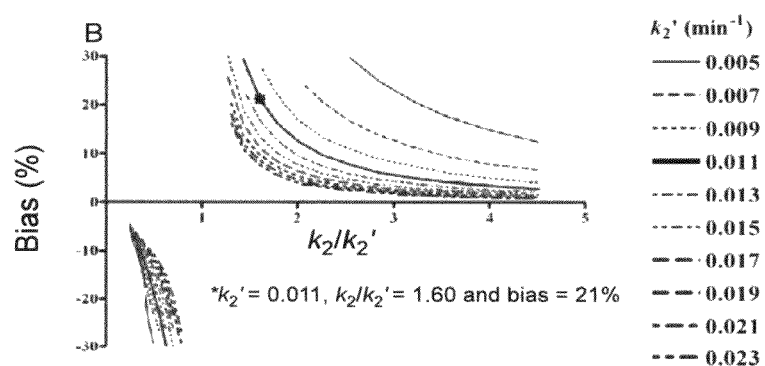
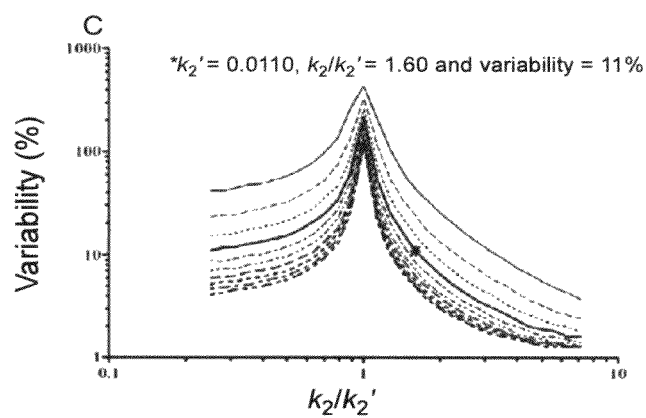

METHODS FOR DIAGNOSING DISEASES AND EVALUATING TREATMENTS THEREFOR USING PET

CROSS-REFERENCE TO RELATED APPLICATIONS

This application is a U.S. National Stage Application of International Application No. PCT/2008/005994, which was filed on May 9, 2008, and which claims priority to U.S. Provisional Application Nos. 60/928,738, which was filed on May 10, 2007, and 60/937,622, which was filed on Jun. 28, 2007, all of which are incorporated by reference in their entireties as if recited in full herein.

GOVERNMENT FUNDING

This invention was made with government support under Grant number 2 RO1 DK63567-03 awarded by the National Institute of Diabetes and Digestive and Kidney Diseases of the National Institutes of Health and Grant number DK077493 awarded by the National Institutes of Health. The government has certain rights in the invention.

FIELD OF THE INVENTION

The field of the present invention relates to diagnosing and evaluating treatment protocols using positron emission tomography (PET) data analysis. More particularly, the present invention relates to diagnosing and evaluating the effectiveness of treatments for, e.g., diabetes, particularly type-1 diabetes, and neurodegenerative diseases, such as, e.g., Alzheimer's Disease. The present invention also relates to monitoring regeneration of islets of Langerhans and the health of transplanted organs, such as the pancreas. The present invention further relates to determining the significant binding capacity of, e.g., the β-cell mass of a pancreas using PET as a measure of the capacity of functioning β-cells.

BACKGROUND OF THE INVENTION

The β-cell mass of the islets of Langerhans in the pancreas is a key factor in determining how much insulin can be secreted for the normal control of blood glucose levels. Non-invasive methods to determine the functional capacity of β-cells are needed to provide, e.g., a biomarker in monitoring the efficacy of novel therapies of, e.g., diabetes, islet regeneration, and pancreas transplantation.

Vesicular monoamine transporter 2 (VMAT2) receptors are expressed by β-cells. Using analogs of tetrabenazine labeled with, e.g., $^{11}C$ or $^{18}F$ (such as [$^{11}C$]dihydrotetrabenazine [DTBZ]) that bind specifically to VMAT2, it has recently been shown that PET has the potential to image binding of the radioligand to VMAT2 in the pancreas. However, there are no known diagnostic PET data analysis tools that are appropriate to quantify the capacity of functioning β-cells in the pancreas.

Thus, there is a need for methods for, e.g., determining the capacity of pancreatic β-cells using PET.

SUMMARY OF THE INVENTION

The present invention is directed to meeting the foregoing and other needs. Thus, one embodiment of the invention is a method of diagnosing diabetes in a patient. This method comprises administering to a patient a positron emission tomography (PET)-compatible tracer, which tracer binds to a vesicular monoamine transporter 2 (VMAT2) receptor, carrying out a PET scan of the patient, and applying a PANC MAP method to the PET scan data to generate a significant binding capacity (SBC) for the patient. In this method, a SBC generated for the patient that is lower compared to a SBC of a control individual who does not have diabetes is indicative that the patient has diabetes.

Another embodiment of the invention is a method for determining whether a mammal has type-1 diabetes. This method comprises calculating significant binding capacity (SBC) from a PET scan of the mammal's pancreas with a radioligand that binds to a vesicular monoamine transporter type 2 (VMAT2) receptor and comparing the SBC of the mammal to a control mammal that does not have diabetes. In this method, a lower SBC in the mammal compared to the control mammal indicates that the mammal has diabetes.

A further embodiment of the present invention is a method for quantifying significant binding capacity (SBC) of a β-cell mass of a pancreas using vesicular monoamine transporter type 2 (VMAT2) positron emission tomography (PET) imaging data. This method comprises: a. applying Module 1 to the VMAT2 PET imaging data, wherein Module 1 comprises: i. identifying binding potential (BP) positive voxels extracted from the PET data; ii. functionally defining a region of interest (ROI) time activity curve (TAC) from the collection of all BP positive voxels identified in step a.i.; b. applying Module 2 to the functionally defined ROI TAC from Module 1, wherein Module 2 comprises: i. applying a three-parameter multilinear reference tissue model (MRTM) to obtain an estimation of a tissue tracer clearance rate ($k'_2$) from a reference tissue, which is kidney cortex; ii. applying a two-parameter multilinear regression analysis (MRTM2) to generate a BP parametric image and a relative blood flow parametric image; and iii. identifying BP positive voxels from the BP and relative blood flow parametric images generated in step b.ii.; and c. applying Module 3 to the BP positive voxels identified in Module 2, wherein Module 3 comprises: i. generating a frequency distribution plot of BP positive voxels from Module 2; and ii. calculating a SBC from the frequency distribution plot of step c.i. for the β-cell mass of the pancreas.

Yet another embodiment of the invention is a method for diagnosing whether a patient has a disease using positron emission tomography (PET) imaging data derived from a PET-compatible tracer that specifically binds to a marker of the disease. This method comprises: a. identifying binding potential (BP) positive voxels extracted from the PET data; b. functionally defining a region of interest (ROI) time activity curve (TAC) from the collection of all BP positive voxels identified in step a; c. applying a three-parameter multilinear reference tissue model (MRTM) to the functionally defined ROI TAC from step b to obtain an estimation of a tissue tracer clearance rate ($k'_2$) from a reference tissue; d. applying a two-parameter multilinear regression analysis (MRTM2) to generate a BP parametric image and a relative blood flow parametric image; e. identifying BP positive voxels from the BP and relative blood flow parametric images generated in step d; f. generating a frequency distribution plot of BP positive voxels from step e; and g. calculating a significant binding capacity (SBC) from the frequency distribution plot of step f. In this method, a difference between the SBC of the patient and a control individual who does not have the disease is indicative that the patient has the disease.

Another embodiment of the invention is a method for diagnosing whether a patient has diabetes. This method comprises applying a PANC MAP method to PET scan data of a patient suspected of having diabetes, wherein if the patient has diabetes, the frequency distribution generated by the PANC MAP method is left-shifted compared to a frequency distribution of a control individual who does not have diabetes.

A further embodiment of the invention is a method for evaluating whether a treatment for diabetes in a patient is effective. This method comprises calculating a significant binding capacity (SBC) from a vesicular monoamine transporter 2 (VMAT2) PET scan of the patient's pancreas before treatment and during or after treatment and determining whether the SBC of the patient during or after treatment has changed compared to the SBC of the patient before treatment. In this method, an increase in the SBC of the patient during or after treatment compared to before treatment is indicative that the treatment is effective.

Another embodiment of the invention is a method for monitoring regeneration of islets of Langerhans in a patient. This method comprises calculating a significant binding capacity (SBC) from vesicular monoamine transporter 2 (VMAT2) PET scans of the patient's pancreas over a period of time and determining whether the SBC of the patient over that period of time has changed. In this method, an increase in the SBC of the patient over that period of time is indicative that the islets are regenerating, a decrease in the SBC of the patient over that period of time is indicative that the islets are degenerating, and no change in the SBC over that period of time is indicative that the islet number is remaining constant.

A further embodiment of the invention is a method for monitoring the health of a transplanted pancreas in a patient. This method comprises calculating a significant binding capacity (SBC) from vesicular monoamine transporter 2 (VMAT2) PET scans of the patient's pancreas over a period of time and determining whether the SBC of the patient over that period of time has changed. In this method, an SBC that remains the same or increases over that period of time is indicative that the transplanted pancreas is healthy, whereas an SBC that decreases over that period of time is indicative that the transplanted pancreas is not healthy.

BRIEF DESCRIPTION OF THE DRAWINGS

The application contains at least one drawing executed in color. Copies of this patent and/or application publication with color drawing(s) will be provided by the Office upon request and payment of the necessary fee. The following drawings form part of the present specification and are included to further demonstrate certain aspects of the present invention. The invention may be better understood by reference to one or more of these drawings in combination with the Detailed Description of the Invention and the Example presented herein.

FIG. 3A is a graph showing Brain ROI Time Activity Data. FIG. 3B is a graph showing Arterial Blood ROI Time Activity Data. The brain time activity curves reflect regional blood flow, plasma tracer clearance, and regional receptor (transporter) density.

FIG. 5 is a schematic illustrating the problems with quantification of pancreatic β-cell mass with [$^{11}$C]DTBZ. Quantification is an outcome measure-β-cell mass (not mean BP); the pancreas is a heterogeneous organ, which consists of exocrine and endocrine as well as fat tissues. What is needed is a voxel-wise BP map. But, voxel TAC can be noisy. Thus, a non-fitting BP map is needed, which is a non-invasive. FIG. 5A is an MRI showing the volume and map of organs, including pancreas (PAN), liver (LIV), stomach (STO), and artery (ART). FIGS. 5B and 5C show VMAT2 stained islet(s) surrounded by non-staining tissue.

FIG. 7 shows [$^{11}$C]DTBZ Data Analysis in two individuals (FIGS. 7A and 7B, respectively) who were each administered a 20 mCi bolus injection of [$^{11}$C]DTBZ followed by dynamic PET imaging of the pancreas and left kidney for 90 minutes.

FIG. 9A shows that non-fitted BP images allow identification of VMAT2 positive voxels. FIG. 9B shows that early summed images allow separation of pancreatic voxels from those voxels in the bowel loops (bile activity).

FIG. 10 shows MRTM2 and general tracer conditions. As FIG. 10A (bias) and 10B (variability) demonstrate, MRTM2 is exceptionally well suited for, e.g., [$^{11}$C]DTBZ pancreatic imaging.

FIG. 11A (BP) and B (R) show images of the pancreas generated using the MRTM2 method.

FIG. 15 shows frequency distribution maps of BP in individuals affected with type-1 diabetes (T1DM) (FIGS. 15A and 15C) compared to normal (control) individuals without the disease (FIGS. 15B and 15D).

FIG. 16A is a FACS analysis with insulin and VMAT2 antibodies. FIGS. 16B and C are frequency distribution maps of BP in those voxels with a BP>0 in normal (control) (16B) and type-1 diabetic (T1DM) (16C) individuals.

FIG. 21 is a flow diagram of Module 2 according to the present invention.

FIG. 22 is a flow diagram of Module 3 according to the present invention.

FIG. 25 shows a perfect 1T TAC ($\alpha=0$ and $\beta=0$, solid line) and a slightly discrepant 1T TAC ($\alpha=0.01$ and $\beta=5$, solid circle) simulated according to Equation 3 using the parameter values for thalamus in Table 2 (FIG. 25A). The bias (FIG.

25B) and variability (FIG. 25C) of $k'_2$ at target region noise of 1.5% in the $k_2/k'_2$ parameter space are shown when $\alpha=0.01$ and $\beta=5$. The $k'_2$ figure key in FIG. 25B also applies to FIG. 25C.

DETAILED DESCRIPTION OF THE INVENTION

The methods of the present invention allow quantification and mapping of disease states, which may be diagnosed, monitored, and/or whose treatments may be monitored using PET data analysis. The present invention has utility in, e.g., diagnosing and/or monitoring a number of diseases for which PET-compatible tracers (e.g., $^{11}$C or $^{18}$F-labeled DTBZ or fluorescently labeled Pittsburgh Compound-B (PIB)), are available for and are specific to a particular marker for the disease, such as decreased β-cell mass in diabetes, particularly type-1 diabetes ($^{11}$C or $^{18}$F-labeled DTBZ) or the presence of β-amyloid plaques in neurodegenerative disorders, such as, e.g., Alzheimer's Disease (fluorescently labeled PIB). With respect to quantification and mapping of functioning β-cell mass in the pancreas, the present methods are referred to as "PANC MAP".

The implication of this invention is that this diagnostic/monitoring/evaluation technique will be an essential tool as PET imaging of, e.g., the β-cell mass becomes widely available. Moreover, the methods of the present invention are particularly useful because conventional PET image data analysis methods do not provide accurate quantification of, e.g., the functioning pancreatic β-cell mass. The methods of the present invention are described herein, as applicable, in comparison with conventional methods for quantification of neuroreceptor binding, such as, VMAT2 binding in the brain.

Figure 1:
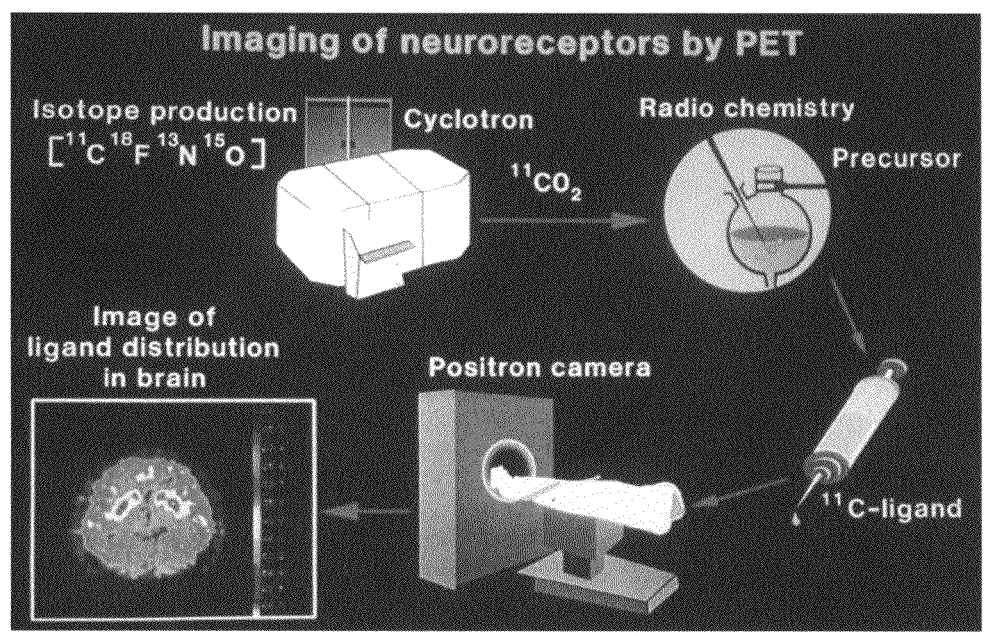
FIG. 1 is a schematic showing the imaging of neuroreceptors by PET.
Figure 2:
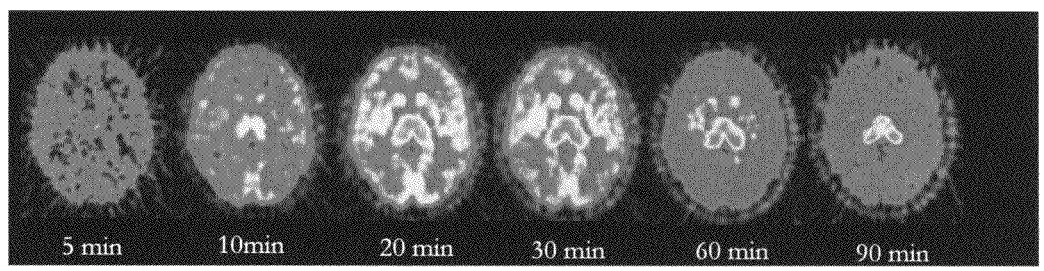
FIG. 2 is a scan showing dynamic PET data.

Conventionally, the outcome measure of neuroreceptor binding from image data is an index of specific binding of neuroreceptors such as VMAT2, which reflects the density of the neuroreceptor in anatomically defined regions of interest (ROIs) such as the striatum of the brain. (FIG. 1). Anatomical ROIs are defined on magnetic resonance imaging (MRI) or computed tomography (CT) data coregistered onto PET or single photon emission tomography (SPECT) data (SPECT also allows VMAT2 imaging when an appropriate radioligand is available).

Figure 4:
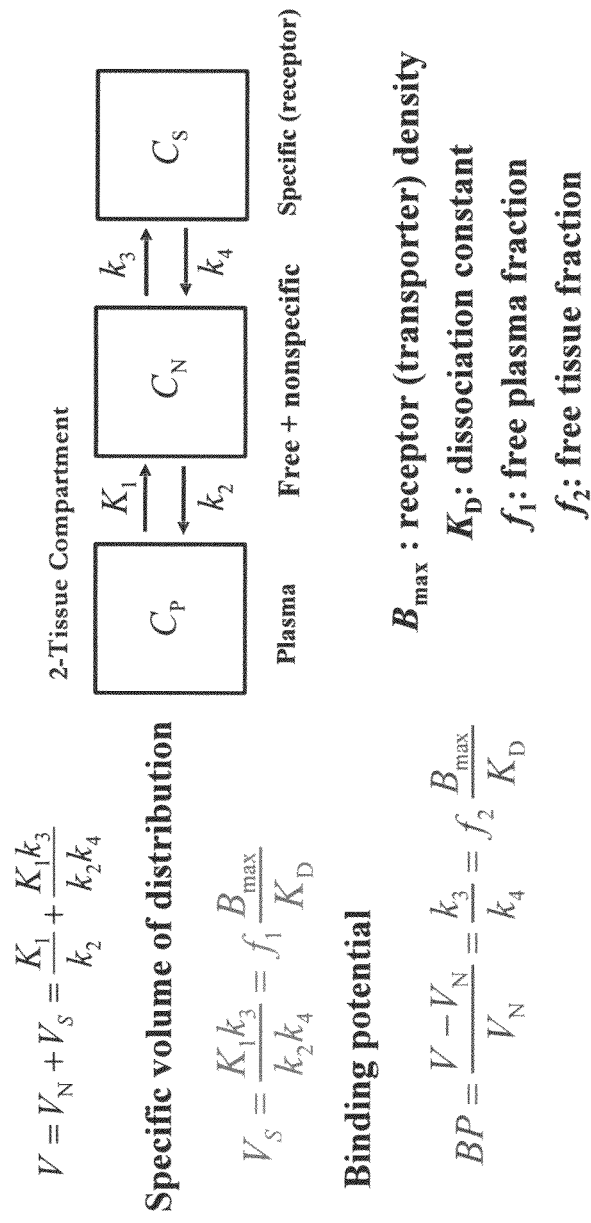
FIG. 4 is a schematic showing Distribution Volumes (V) and Binding Potential (BP) calculations.

One way to quantify specific binding or binding potential (BP) is to first extract the mean time activity curve (TAC) of ROIs from PET or SPECT data and then estimate BP from these TACs with or without radioligand TAC in plasma by using a compartment kinetic model. (See, e.g., FIGS. 3 and 4). Alternatively, as opposed to ROI TACs, voxel (the smallest volume element in the image data) TAC can be used for this purpose, although the latter approach is often compromised due to more noise in the voxel TAC than in the ROI TAC. Either way, the conventional outcome measure is the mean BP in anatomically defined ROIs. (FIG. 5).

Quantification of VMAT2 binding of the pancreas is different from that of the brain, because the pancreas contains both the exocrine and endocrine (β-cell) tissue components where VMAT2 is predominantly expressed by the β-cells. (FIG. 5B). ROIs as defined by magnetic resonance imaging (MRI) or computed tomography (CT) include these two tissue components as well as fat tissue. However, these anatomical imaging tools (MRI and CT) cannot distinguish between the two tissue types, exocrine and endocrine (β-cell) tissues. The most relevant and important information needed from VMAT2 PET image data is a quantitative measure that reflects total VMAT2 sites within the pancreas in the light of the hypothesis that this VMAT2 measure reflects functioning β-cell mass, which is, in turn, thought to be a key determinant of insulin secretion capacity of the pancreas. In addition, recent evidence suggests that there may be a threshold of VMAT2 density below which insulin secretion capacity is impaired.

The above considerations about VMAT2 quantification in the pancreas necessitate a PET data analysis tool (strategy) that allows for the voxel-wise mapping of VMAT2 density (BP) without the use of anatomically defined ROIs and a tool (strategy) that allows profiling of all VMAT2 binding voxels according to voxel BP values. The PANC MAP method described in more detail below accomplishes both of these two goals. Both strategies used herein are novel and unexpectedly useful in determining, e.g., β-cell mass. The methods of the present includes three modules. Although these three modules may be implemented in basic well known and/or commercially available computational software such as, e.g., MATLAB (such as, e.g., R2007a, which includes MATLAB 7.4 from The MathWorks, Inc., Natick, Mass.), the methods of the present invention, including the PANC MAP method, may be programmed into a dedicated easy-to-operate diagnostic software package using the information disclosed herein.

Generally, the present invention includes three modules. Modules 1 and 2 allow generation of a three-dimensional map of tracer, e.g., radioligand, binding and Module 3 allows profiling of voxel-wise distribution of the tracer, e.g., radioligand, binding. Thus, for example, with respect to PANC MAP, Modules 1 and 2 allow generation of a three-dimensional map of VMAT2 binding and Module 3 allows profiling of voxel-wise distribution of VMAT2 binding. In the present invention, Modules 1, 2, and 3 may be used together. Other combinations of the modules, however, may also be used in the present invention, such as for example, Module 1 and Module 3.

The conventional neuroreceptor binding measure is the mean BP over anatomically defined ROIs. In the present invention, a new outcome measure of VMAT2 binding in the pancreas has been defined and quantified. The new definition is as follows:

Significant Binding Capacity (SBC)=Σ(individual voxel BP above predetermined significant value× voxel volume)

(the unit is volume (e.g., mL) because BP is unitless). Thus, SBC is the outcome measure that should reflect total β-cell capacity (volume) of significance. In the present invention, the predetermined significant value may be, for example, a BP value greater than zero.

Module 1—Non-Fitting Voxel-Wise Parametric Mapping

Figure 6:
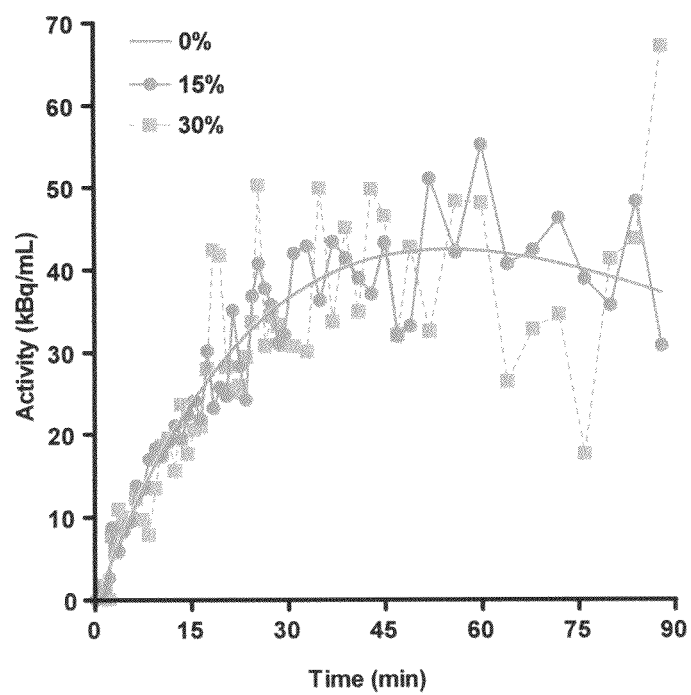
FIG. 6 is a graph plotting ROI vs. Voxel TACs.

As mentioned above, creation of voxel-wise parametric BP images can be problematic because voxel TACs are noisy compared to ROI TACs. (FIG. 6). For most PET tracers, e.g., radioligands, however, estimation of BP according to a kinetic model is needed because TACs themselves represent the combined effects of dose of the radioligand administered, blood flow, weight of individuals, VMAT2 binding, and tracer, e.g., radioligand, clearance from plasma. Therefore, TACs even when they are normalized by the injected dose of the tracer, e.g., radioligand, and subject weight, do not accurately reflect VMAT2 binding. In particular, blood flow to the pancreas is significantly reduced in type-1 diabetics. BP estimated by the kinetic model based method, however, is independent of all of these additional factors.

Figure 8:
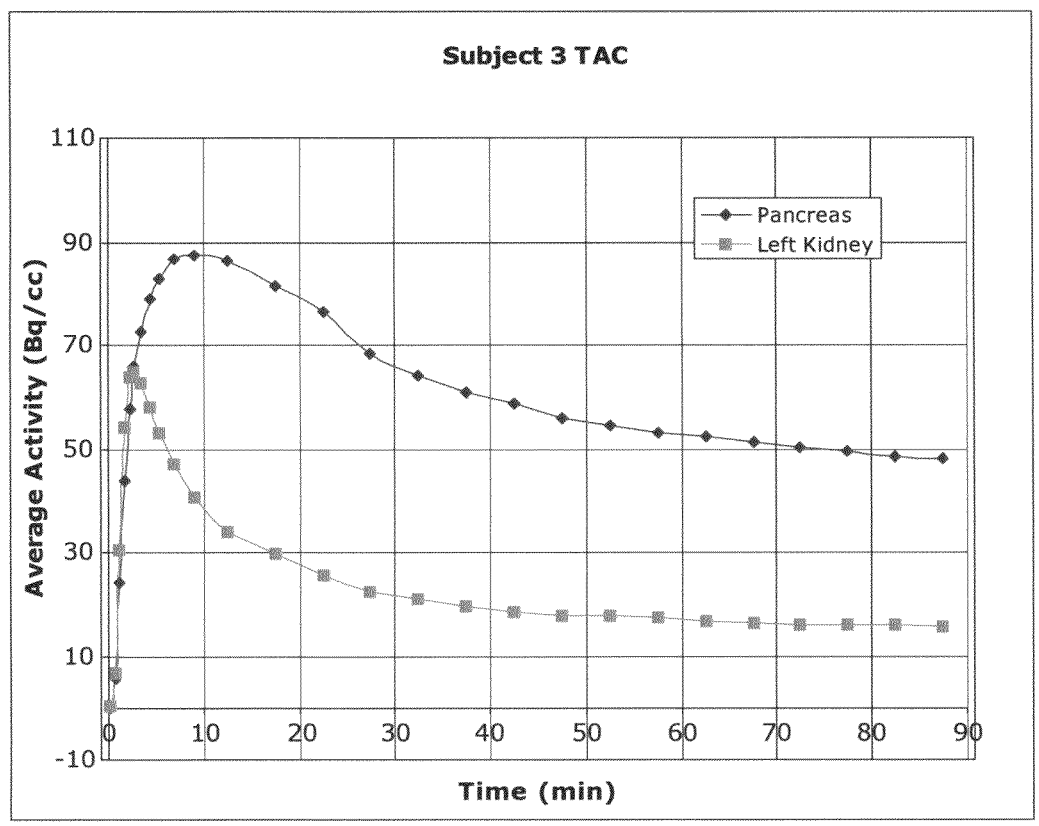
FIG. 8 is a graph showing the pseudo or transient equilibrium approach (Module I), wherein $C_{pancreas}/C_{kidney}$-constant, where $BP = AUC_{pancreas}$ (30-90 min)/$AUC_{kidney}$ (30-90 min)−1.
Figure 20:
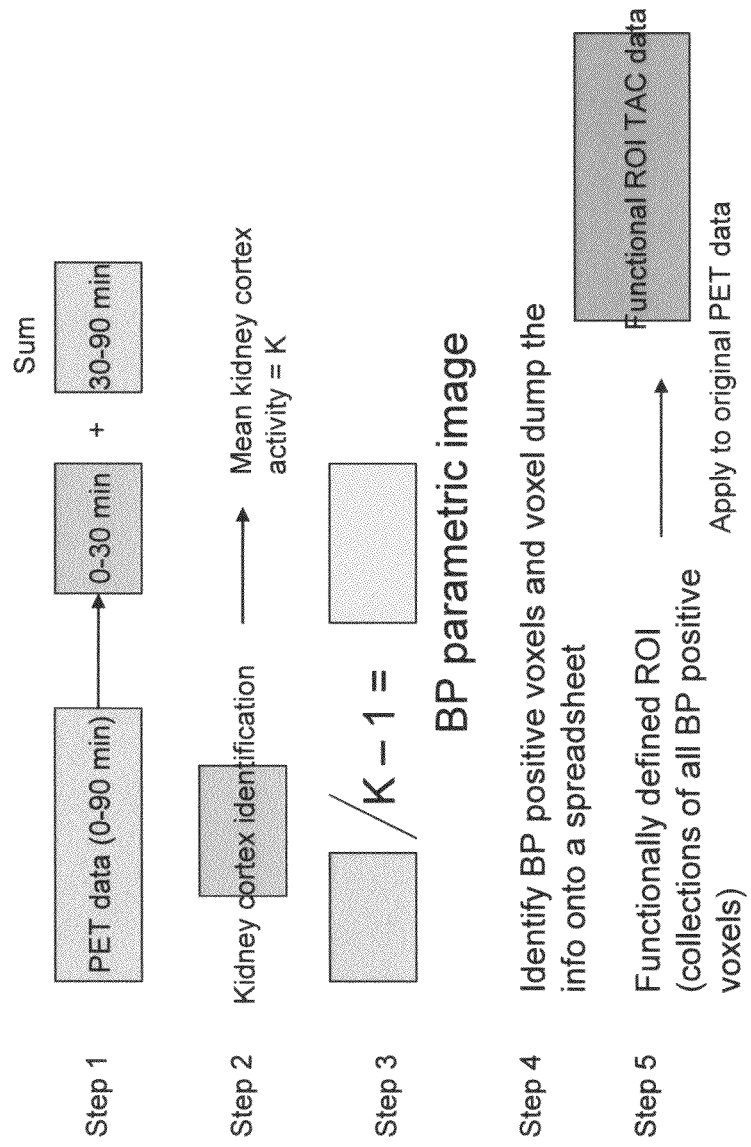
FIG. 20 is flow diagram of Module 1 according to the present invention.

One approach is not to use data fitting techniques based on a kinetic model. For example, if a target TAC decreases over time beyond a certain time point at the same rate as a reference TAC, the tissue ratio can be used as a receptor parameter, although, theoretically, this ratio overestimates true BP. This strategy is possible with certain tracers under certain conditions. This property depends on the tracer. [$^{11}$C]DTBZ, however, appears to satisfy this condition. Indeed, DTBZ TACs follow a condition called transient equilibrium at certain time points; although BP measured during this period without model fitting of TAC data theoretically overestimates true BP. (FIG. 8). However, if the overestimation is a systematic overestimation, i.e., the same degree of overestimation across the range of BP, this non data fitting approach will work as an outcome measure. Module 1 generates voxel-wise mapping of BP without mathematical model fitting the PET data. A flow diagram of the procedure to carry out Module 1 is set forth in FIG. 20.

Although Module 1 may work well for [$^{11}$C] DTBZ and other related VMAT2 PET/SPECT tracers in all subjects to generate voxel-wise mapping of BP (called parametric images of BP), Module 2, which is based on a mathematical model should be more accurate. Module 1, however, should be performed first, because it generates BP parametric images without defining the pancreas ROI and these BP images allow identification of all BP positive VMAT2 containing voxels. Then, VMAT2 positive ROIs (sum of all voxels with BP>0) may be defined on a spreadsheet by voxel-dumping the information on the BP parametric images (three-dimensional position of each voxel and its BP value). This technique will, in turn, allow generation of the functionally defined β-cell ROI TAC from the original PET data, which can also be used for Module 2 (see below). As shown in the flow diagram in FIG. 20, Module 1 requires identification of kidney cortex, which is accomplished by summing those PET images in the early time course, which reflects blood flow (kidney blood flow is very high).

Module 2—Voxel-Wise Fitting Method

Another approach is noise resistant parametric imaging with model fitting of voxel TACs, which is more accurate than Module 1 parametric images. A noise resistant parametric imaging method for voxel-wise estimation of BP without plasma data called MRTM2 was previously developed and applied to brain imaging of serotonin transporters. See, Ichise M, Liow J-S, Lu J-Q, Takano A, Model K, Toyama H, Suhara T I Suzuki K, Innis R B, and Carson R E. Linearized reference tissue parametric imaging methods: Application to [$^{11}$C] DASB positron emission tomography imaging of the serotonin transporter in human brain. J. Cereb Blood Flow Metab., 23:1096-1112 (2003), which is incorporated by reference as if recited in full herein. This method requires a priori estimation of the reference tissue clearance rate, k2', by using another related model called MRTM. (Id.).

Figure 12:
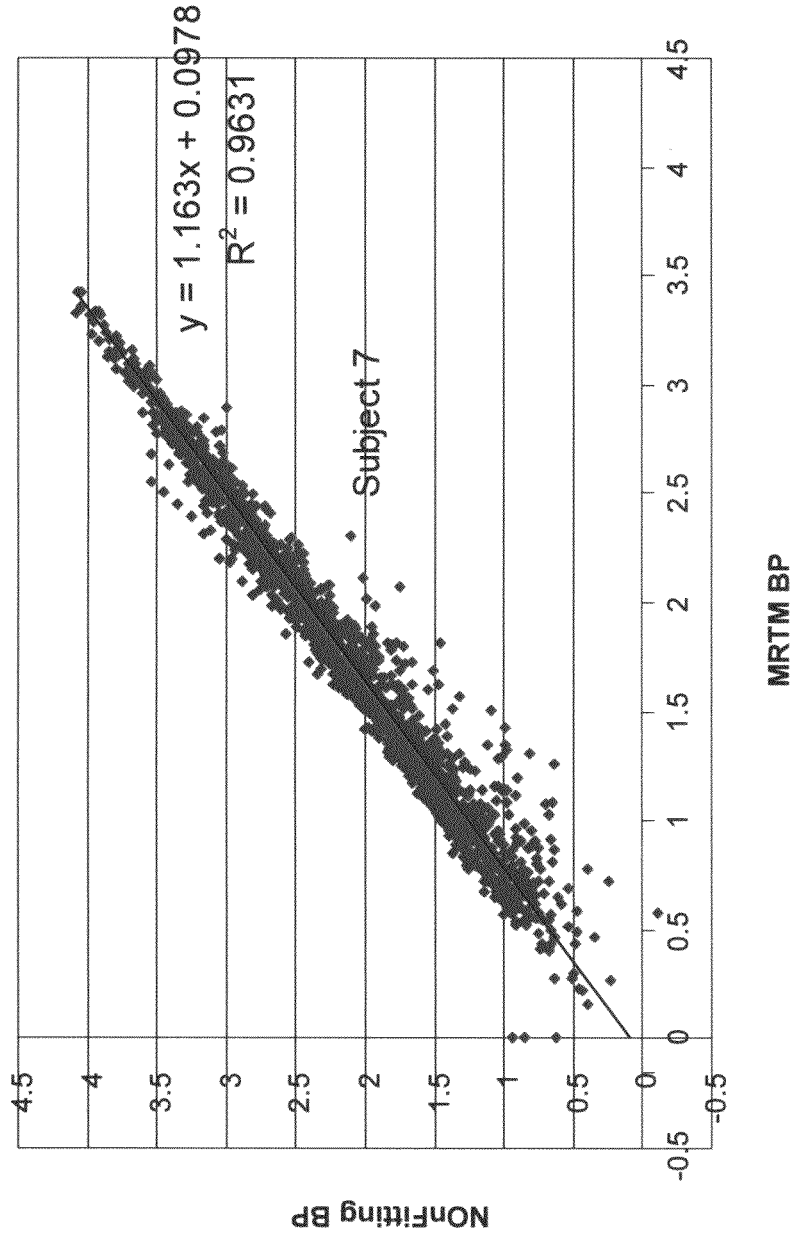
FIG. 12 shows a graph of Voxel MRTM BP vs. Non-fitting BP.
Figure 13:
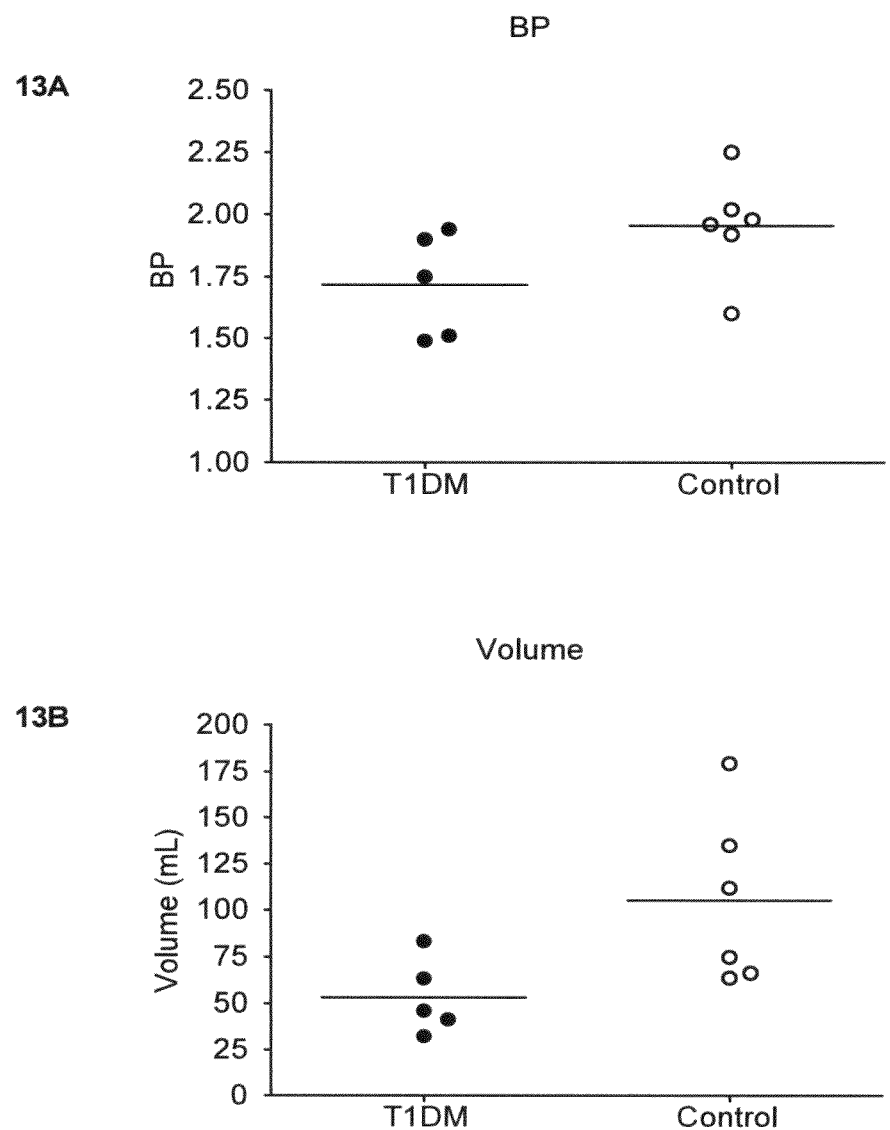
FIG. 13A shows a graph of BP in an individual with type-1 diabetes compared to a normal (control) individual without the disease.
FIG. 13B is a graph of Volume in an individual with type-1 diabetes (T1 DM) compared to a normal (control) individual without the disease.
Figure 14:
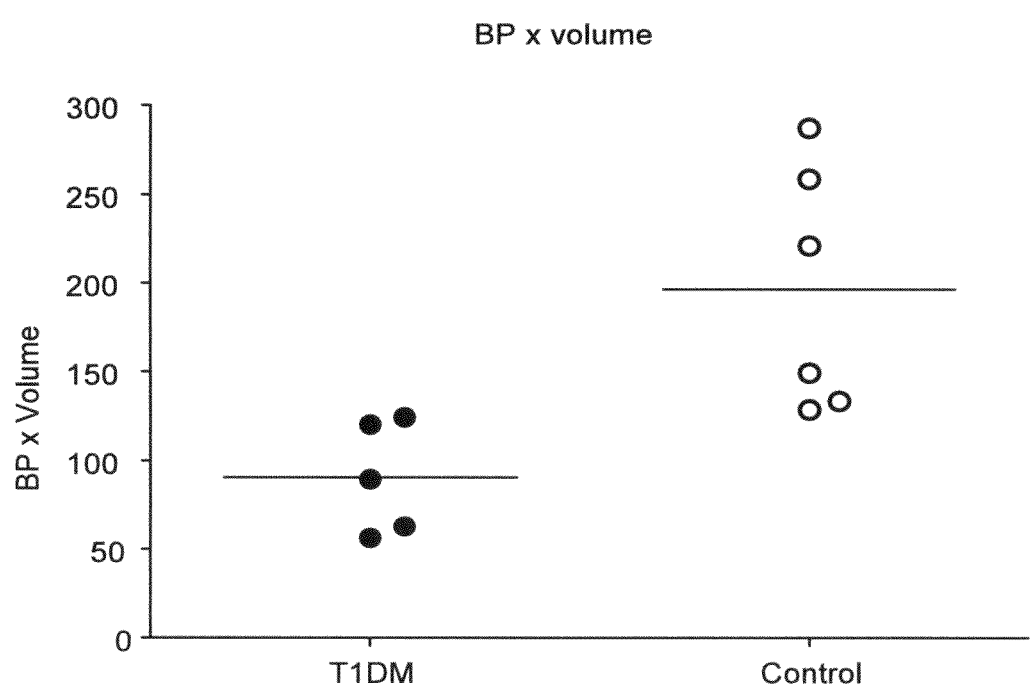
FIG. 14 shows a graph of BP×Volume in an individual with type-1 diabetes (T1 DM) compared to a normal (control) individual without the disease.
Figure 16:
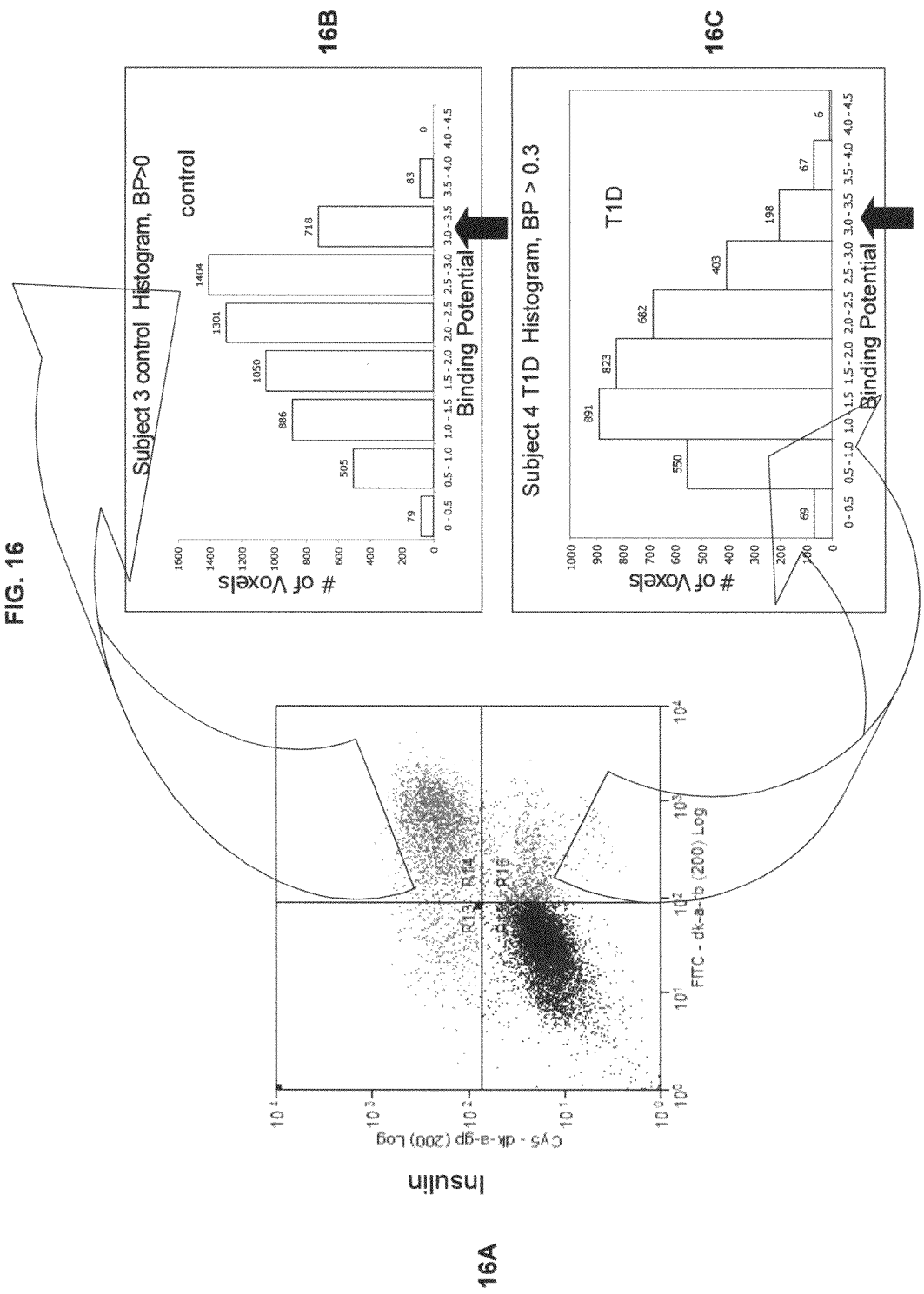
FIG. 16 is a graphic showing the relationship between insulin producing capacity and VMAT2 receptor density.
Figure 17:
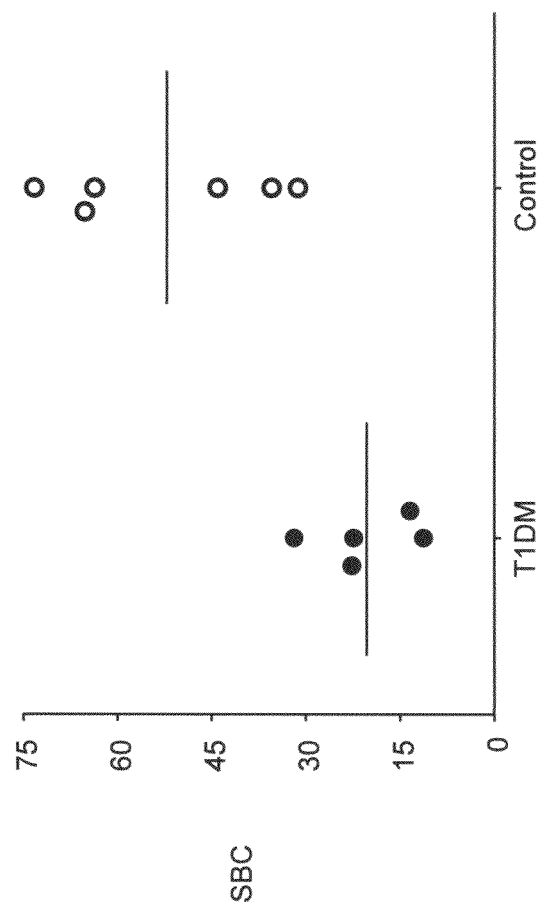
FIG. 17 is a graph of SBC in an individual affected with type-1 diabetes (T1 DM) compared to a normal (control) individual without the disease.
Figure 18:
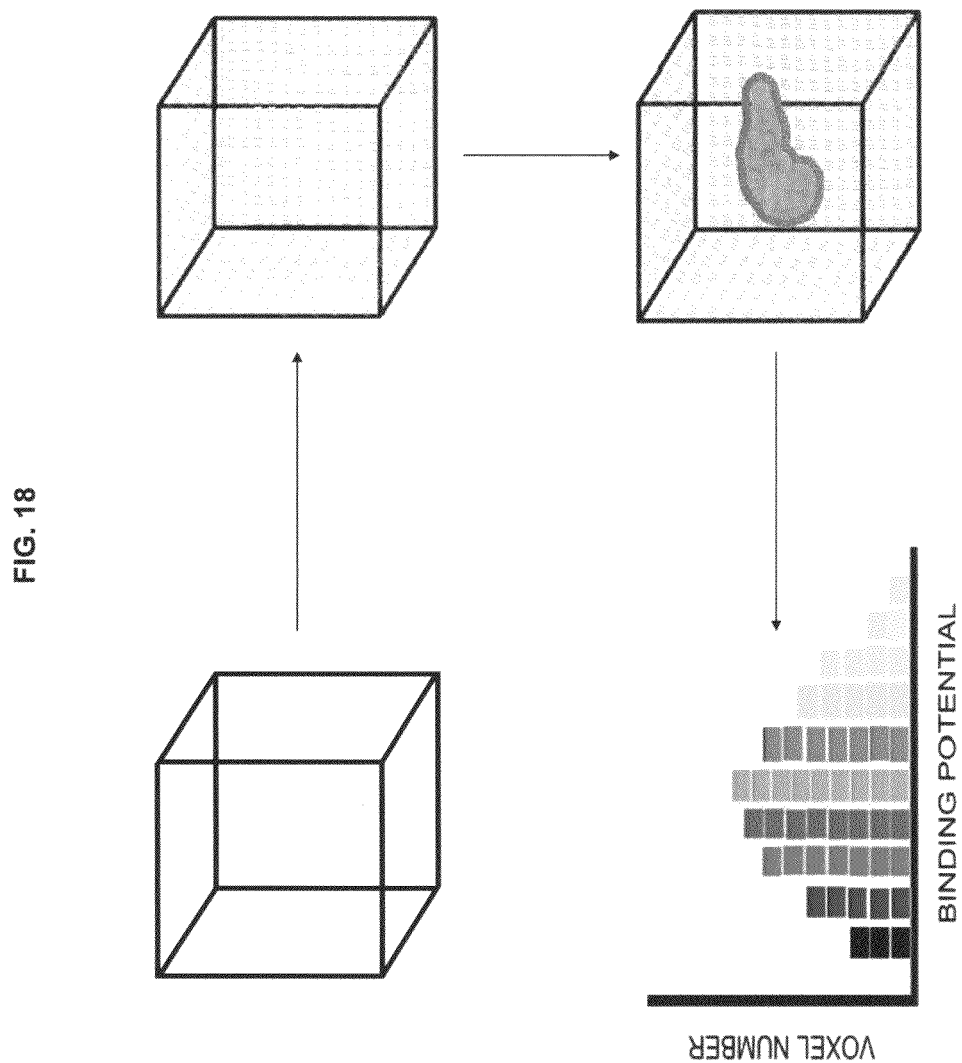
FIG. 18 is a schematic summarizing the PANC MAP method.
Figure 19:
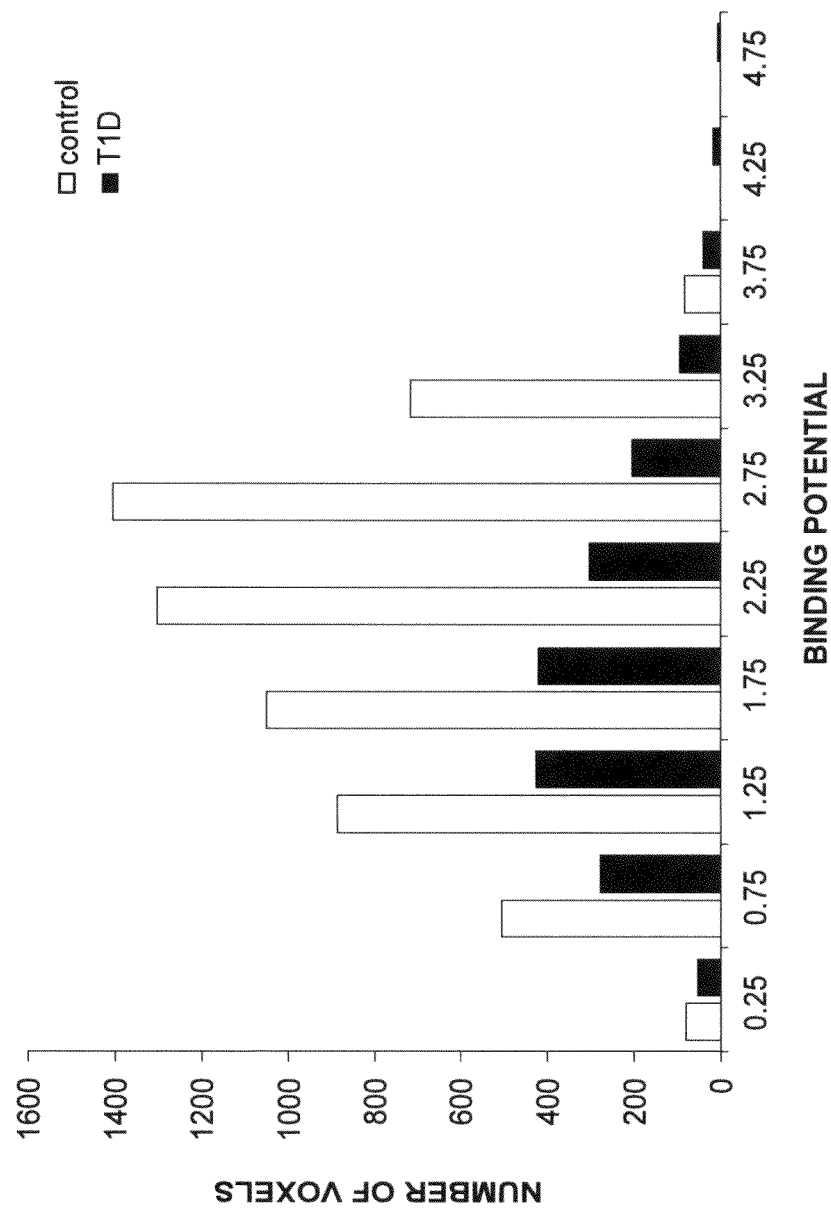
FIG. 19 is graph showing that healthy controls and type-1 diabetes (T1 D) patients have different BP profiles.

The MRTM2 method provides the most noise resistant and unbiased parametric images of BP if certain conditions are met. Unexpectedly, these conditions are exceptionally well met for DTBZ and the bias and variability of voxel BP by this method is less than 1-2 percent. (See Example 1 and FIG. 10). Thus, either the non-fitting or the MRTM2 method is suited for DTBZ PET data analysis of the pancreas. (FIG. 12). However, the MRTM2 additionally gives relative blood flow parametric images which can help to identify VMAT2 voxels on BP images. (FIG. 11).

MRTM2 parametric imaging provides accurate VMAT2 BP images as well as relative blood flow parametric images. The MRTM2 method requires, in the initial step, k2' estimations by MRTM using ROI TAC data. Functionally defined ROI TAC data (not BP data) obtained in Module 1 is used for this purpose. A flow diagram of the procedure to carry out Module 2 is set forth in FIG. 21.

Module 3—Profiling of Voxel VMAT2 BP and Determination of SBC

In order to obtain SBC, profiling of individual voxel BPs is needed. This can be accomplished by presenting the results of the voxel BP data in a frequency distribution plot of BP. Frequency distribution analysis of DTBZ voxel BP data showed that type-1 diabetes (T1D) patients had clearly different (i.e., left-shifted) voxel VMAT2 BP profiles compared to normal controls. (FIGS. 15-19). This type of voxel BP profiling has not been performed in conventional neuroreceptor PET data analysis. A flow diagram of the procedure to carry out Module 3 is set forth in FIG. 22.

Thus, the present invention, more particularly the PANC MAP method, is a new diagnostic tool for the quantification of SBC of the β-cell mass of a pancreas from VMAT2 PET imaging data. This tool consists of several new ideas about how the VMAT2 PET data are analyzed to quantify the functioning β-cell mass including (1) generation of a BP map of the pancreas without the use of an anatomically (MRI or CT) defined pancreatic ROI, (2) voxel profiling of VMAT2 binding, and (3) definition of SBC. These ideas are not in the conventional PET data analysis methods. The PANC MAP approach appears essential in the application of VMAT2 imaging to studies of the pancreas. This method also incorporates parametric imaging methods because the incorporation of it is exceptionally well suited for DTBZ analysis. Although this tool currently requires the use of basic software programs, a dedicated single software package, "PANC MAP," may be developed from the information disclosed herein to perform the PET data analysis procedure.

The following examples are provided to further illustrate the methods of the present invention. These examples are illustrative only and are not intended to limit the scope of the invention in any way.

EXAMPLES

Example 1

MRTM2 and MRTM

MRTM2 (two-parameter multilinear regression analysis) uses the following operational equation developed from the tracer kinetic model (Ichise M, et al., J Cereb Blood Flow Met; 23:1096-1112 (2003):

$$C_T(T) = R_1\left(k_2' \int_0^T C_T'(t)\,dt + C_T'(T)\right) - k_2 \int_0^T C_T(T)\,dt \quad \text{Equation 1}$$

Parametric imaging of BP requires initial estimation of k2' (tissue tracer clearance rate from the reference tissue (kidney cortex in the present case)). This k2' is a single value needed to plug into Equation 1 before performing voxel-wise parametric imaging. k2' estimation requires two ROI TACs and MRTM (multilinear regression analysis). (Id.). The MRTM operational equation is $$C_T(T) = R_1 k_2' \int_0^T C_T'(t)\,dt - k_2 \int_0^T C_T(t)\,dt + R_1 C_T'(T) \quad \text{Equation 2}$$

In PANC MAP (module 2), functionally defined ROI TACS (β-cell pancreas and kidney cortex) from Module 1 are used as opposed to the conventional MRI or CT defined ROIs. This concept of functionally defined ROI is a new idea in PANG MAP.

The accuracy of BP on MRTM2 parametric images depends on how accurately one can determine $k_2'$. This accuracy expressed in terms of bias and variability of $k_2'$ estimations, is shown graphically in FIGS. 10A and 10B, respectively. Unexpectedly, it turns out that for VMAT2 imaging with [$^{11}$C]DTBZ, $k_2'$ can be estimated exceptionally well with both the bias and variability<1-2% (see FIGS. 10A and 10B).

Example 2

Evaluation of Accuracy of $k_2'$ Estimation by MRTM

A. MRTM $k_2'$ Using Neuroreceptor Ligand[$^{18}$F]FP-TZTP

An F-18 labeled muscarinic-2 (M2) subtype-selective agonist, 3-(3-(3-[18F]Fluropropyl)thio-1,2,5-thiadiazol-4-yl)-1,2,5,6 tetrahydro-1-methylpyridine ([$^{18}$F]FP-TZTP), has been successfully used for positron emission tomography (PET) imaging of central M2 cholinergic receptors in humans. Cohen R M, Podruchny T A, Bokde A L, Carson R E, Higher in vivo muscarinic-2 receptor distribution volumes in aging subjects with an apolipoprotein E-epsilon4 allele. Synapse 49:150-156 (2003). Kinetic modeling studies of [$^{18}$F]FP-TZTP PET data have shown that [$^{18}$F]FP-TZTP time-activity data can be described by the one-tissue (1T) compartment model with two kinetic rate constants, $K_1$ (mL/min/cm$^3$, the rate constact for transfer from plasma to the tissue) and $k_2$ (min$^{-1}$, the tissue clearance rate constant). Carson R E, Kiesewetter D O, Jagoda E, Der M G, Herscovitch P, Eckelman W C, Muscarinic cholinergic receptor measurements with [$^{18}$F]FP-TZTP: control and competition studies. J Cereb Blood Flow Metab 18:1130-42 (1998); Carson R E, Kiesewetter D O, Connely K. Mentis M J, Cohen R M, Herscovitch P, Sunderland T, Eckelman, W C, Kinetic analysis of the muscarinic cholinergic ligand [F-18]FP-TZTP in humans. J Nucl Med 40:30P (1999).

Figure 23:
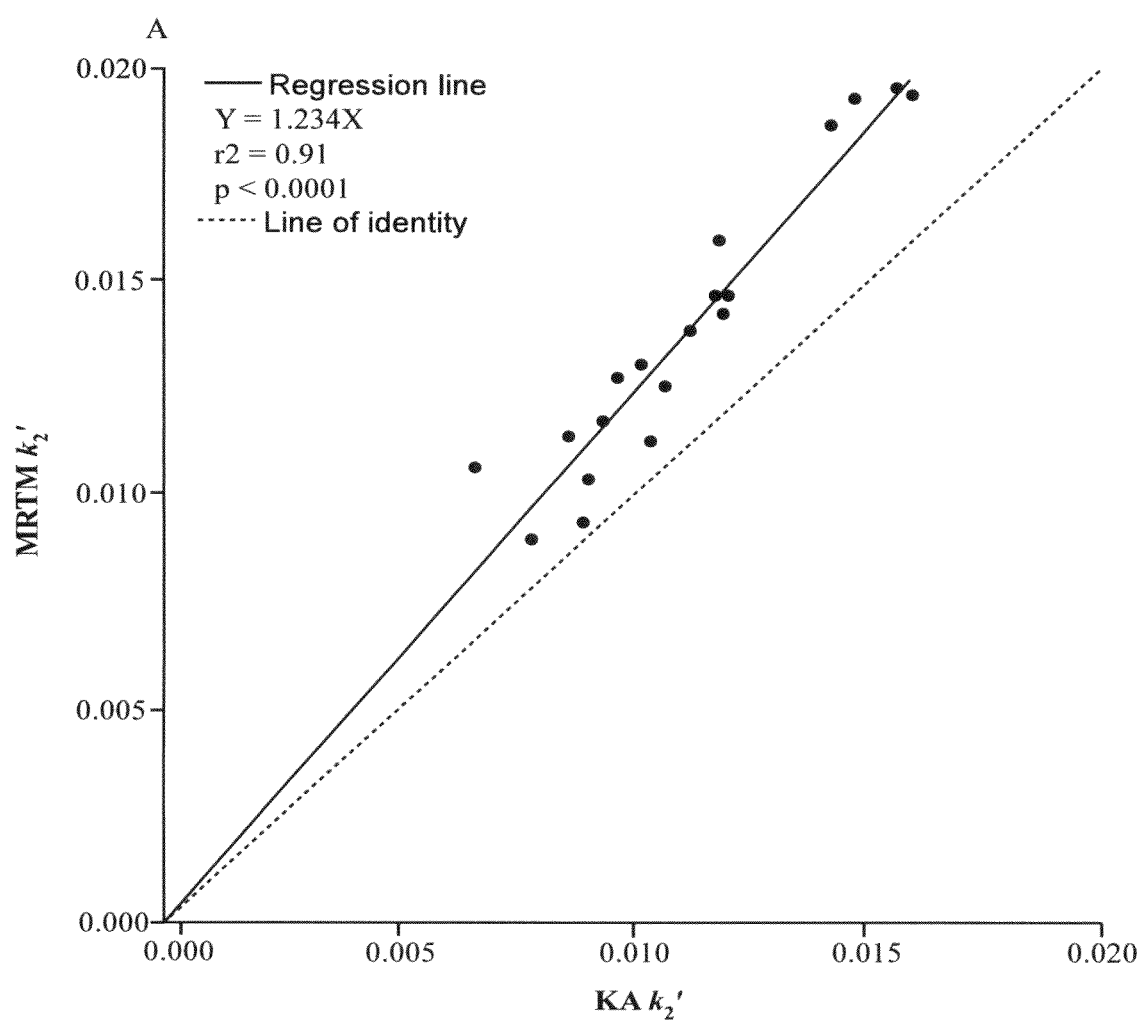
FIG. 23 shows the relationships between $k'_2$ estimated by the 3-parameter multilinear analysis (MRTM) using [$^{18}$F]FP-TZTP and one-tissue kinetic analysis (1TKA).

In a PET study using [$^{18}$F]FP-TZTP (data not shown), MRTM $k'_2$ was positively biased by 24%, i.e., the MRTM $k'_2$ values were 24% higher than those estimated by 1TKA, with a strong positive linear correlation between the two methods of estimation. FIG. 23 shows the relationships between $k'_2$ estimated by the 3-parameter multilinear analysis (MRTM) and one-tissue kinetic analysis (1TKA). The MRTM $k'_2$ bias for the simulated data and that for the [$^{18}$F]FP-TZTP data were not consistent with each other.

B. Simulation Analysis Method

Computer simulation analysis was performed to evaluate the accuracy of $k'_2$ estimation by MRTM using ROI TAC data. The steps taken for the simulation analyses are outlined in Table 1.

TABLE 1

Simulation Analysis Steps

| Step | Procedure |
|---|---|
| 1 | Calculation of group mean 1TKA parameter values for the cerebellum and thalamus (Table 2) |
| 2 | Calculation of group mean thalamus TAC noise (1.5%, Table 2) |
| 3 | Generation of noise-free 1TKA TACs (cerebellum and thalamus) using the parameters derived from the group mean parameter values (Table 2) (total of 10 cerebellum TACs and 10 × 30 thalamus TACs in the $k_2/k'_2$ space) |
| 4 | For each thalamus TAC, 1,000 TACs were generated by adding random noise of 1.5% |
| 5 | Evaluation of the bias and variability of $k'_2$ estimations using noise-free cerebellum TACs and noisy thalamus TACs in the $k_2/k'_2$ |
| 6 | Generation of another set of 10 × 30 thalamus TACs as in Step 3 but TACS are perturbed with an addition of another tissue compartment (Section D below) |
| 7 | Repeat Step 4 to generate noisy thalamus TACs from those discrepant TACs generated in Step 6 |
| 8 | Repeat Step 5 to evaluate the bias and variability of $k'_2$ estimations using noise-free cerebellum TACs and noisy and discrepant thalamus TACs in the $k_2/k'_2$ |

1TKA, one-tissue kinetic analysis; TAC, time-activity curve.

TABLE 2

One-tissue compartment kinetic parameter values and % noise of time-activity curve derived from the mean of 11 subjects and used for computer simulation analysis.

| Region | $K_1$ (mL/min/cm$^3$) | $K_2$ (min$^{-1}$) | $V_T$ (mL/cm$^3$) | $k_2/k'_2$ | Noise (%) |
|---|---|---|---|---|---|
| Cerebellum* | 0.466 | 0.0110 | 43 | — | — |
| Thalamus | 0.506 | 0.0176 | 29 | 1.60 | 1.5 |

*The $K_1$, $k_2$ and $V_T$ values for cerebellum (input region) refer to those of $k'_1$, $k'_2$ and $V'_T$, respectively.

Step 1: To calculate group mean parameter values that can be used for computer simulation analysis, ROI TACs were fitted by one-tissue kinetic analysis "1TKA" using individual metabolite-corrected plasma input functions. The mean 1TKA parameter values from 11 subjects were then used to generate noise-free TAC data as described below in Step 3.

Step 2: ROI TAC percent noise was calculated based on deviations from 1TKA fitting (100×SD/mean) for the latter portion of the TAC (60 to 120 min) and the mean percent noise over these 11 subjects was calculated (Table 2).

Step 3: Preliminary simulation analysis suggested that the bias and variability of MRTM $k'_2$ estimation at a typical ROI noise level are dependent on the $k_2/k'_2$ ratio and the magnitude of $k'_2$. Therefore, 1T TAC data were simulated in the $k_2/k'_2$ parameter space. To this end, one typical metabolite-corrected plasma input was selected from the subject group, and was scaled to a group mean injected dose of 10.2 mCi. Noise-free TACs for cerebellum (input region) and thalamus (target region) were simulated using the 1T parameter values derived from the group mean $K_1$ and $k_2$ values (n=11) estimated by 1T KA for the respective regions (Table 2) for 120 min (33 frames, the same sampling as used in actual PET data). Intravascular radioactivity was not included since its contribution would be minimal due to the high rate constant from plasma to the tissue ("$K_1$") and total distribution volume ("$V_T$") values. The thalamus was chosen because $k_2/k'_2$=1.60 was highest. Then, another 9 noise-free cerebellar TACs were generated where $k'_2$ was varied from 0.005 min$^{-1}$ to 0.023 min$^{-1}$ in 0.002 increments, keeping the same value of $k'_1$=0.466 mL/min/mL. Corresponding to each of these 10 cerebellum TACs, 30 thalamus TACs were generated total of 10×30 or 300 TACs), keeping the same value of $k_1$=0.506 mL/min/cm$^3$, but with different values of $k_2$ such that $k_2/k'_2$ varied from 0.25 to 7.14.

Step 4: Then, random amounts of normally distributed mean zero noise were added to the noise-free thalamus TACs using the noise model described previously (Ichise et al., 2003). One thousand noisy TACs were generated for each of thalamus TACs at a noise level of 1.5%, which was the mean % noise of 11 subjects (Table 2) (total of 1,000×300 TACs).

Step 5: The accuracy of $k'_2$ estimation was evaluated by calculating the bias (% deviation of the sample mean (n=1000) from the true value) and the variability (% sample SD relative to the true value). Weighted linear least-squares MRTM fitting was performed with weights equal to the inverse of the simulated data variance.

Step 6: Preliminary simulation analysis suggested that substantial MRTM $k'_2$ bias might be introduced by a slight discrepancy for the 1T model. Therefore, for each of the 10 cerebellum TACs, another set of 30 thalamus TACs were generated in the same manner as above except that another tissue compartment in parallel with the original 1T compartment was added as described in section D below.

Step 7. Step 4 was repeated to generate noisy thalamus TACs from those discrepant TACs generated in Step 6.

Step 8. Step 5 was repeated to evaluate the bias and variability of $k'_2$ estimations using noise-free cerebellum TACs and noisy and discrepant thalamus TACs in the $k_2/k'_2$ space.

All simulation analyses were performed in MATLAB and/or pixel-wise kinetic modeling.

C. Simulation Analysis

Figure 24:
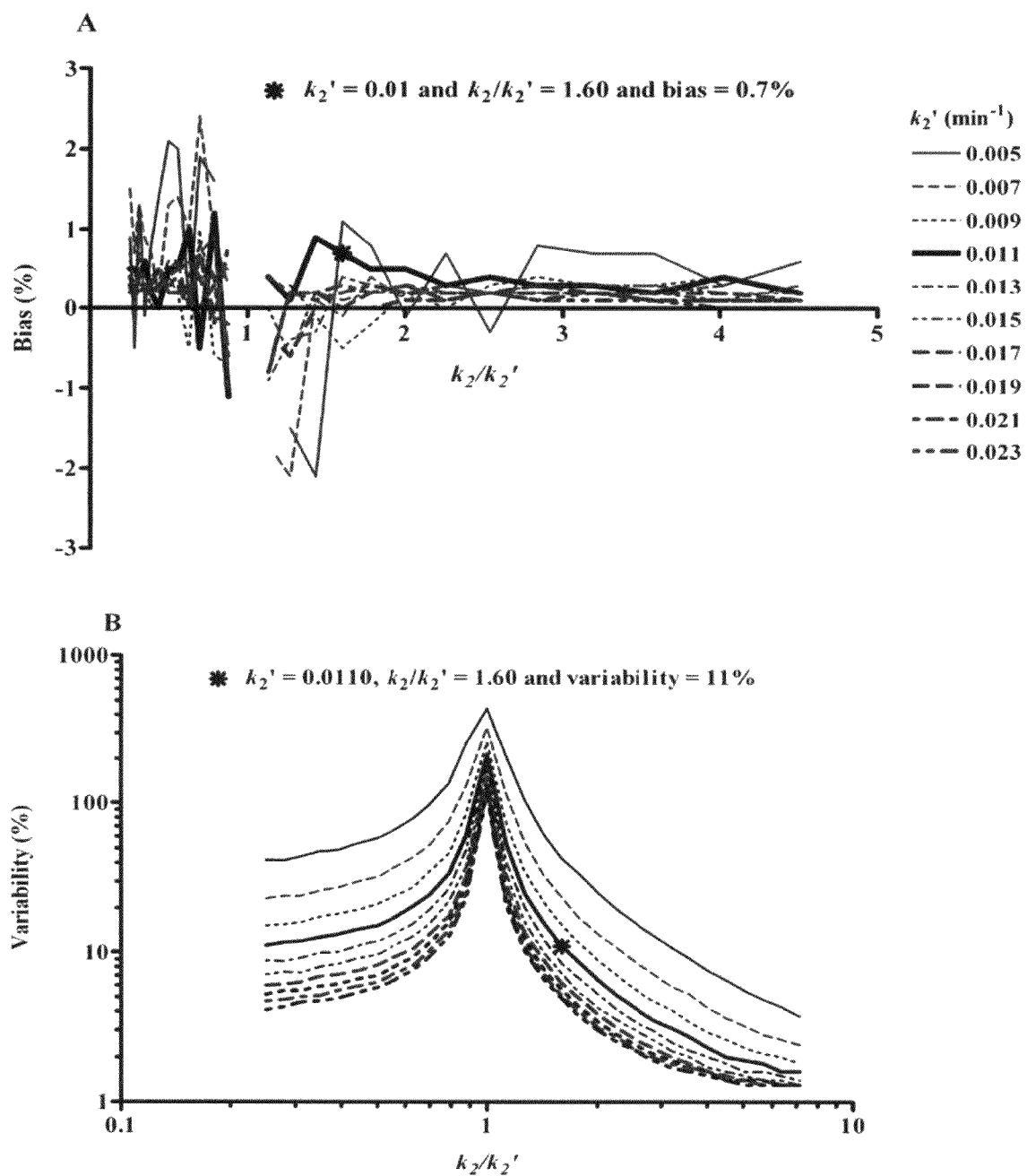
FIG. 24 shows bias (24A) and variability (24B) of $k'_2$ estimation by the three-parameter multilinear reference tissue model (MRTM) at target region noise (thalamus) of 1.5% for simulated time activity data in the $k_2/k'_2$ parameter space. The $k'_2$ figure key in FIG. 24A also applies to FIG. 24B.

FIG. 24 shows bias (24A) and variability (24B) of $k'_2$ estimation by the three-parameter multilinear reference tissue model (MRTM) at target region noise (thalamus) of 1.5% for simulated time activity data with parameter values from Table 2 in the $k_2/k'_2$ parameter space. The bias of $k'_2$ estimation by MRTM was very small at 0.7% (FIG. 24A) and relatively independent of the magnitude of $k'_2$ across the $k_2/k'_2$ parameter space except when $k_2/k'_2$ became very close to unity (bias=130% when $k_2/k'_2$ was unity) (FIG. 24A). The reason for this exceptionally large $k'_2$ bias at $k_2/k'_2$=1 is that Equation 2 becomes unstable when both the input and target regions have the same tissue clearance rate constant ($k'_2=k_2$).

The MRTM $k'_2$ variability was strongly dependent on both the $k_2/k'_2$ ratio and the magnitude of $k'_2$. The $k'_2$ variability increased asymptotically as $k_2/k_2$ approached unity (FIG. 24B). Conversely, the $k'_2$ variability decreased as $k_2/k'_2$ became further away from unity. For example, with $k'_2=0.011$, the variability was 2.3, 11.0 and 230% when $k_2/k'_2$ was 4.0, 1.6 and 1.0, respectively. In addition, the k'2 variability in the $k_2/k'_2$ space decreased progressively as the $k'_2$ value increased (FIG. 24B). For example, with $k'_2=0.023$, the variability was 1.5, 4.9 and 1 18% when $k_2/k'_2$ was 4.0, 1.6 and 1.0, respectively.

In contrast to the case with the data simulated by the perfect 1T model, as described in section D below, the bias of MRTM $k'_2$ estimation for slightly discrepant data (not shown) using [$^{18}$F]FP-TZTP 1T was significantly biased. However, the variability of $k'_2$ estimation was essentially the same for the two data sets. The simulation data for the slightly discrepant 1T model also showed that both the bias and variability of MRTM $k'_2$ estimation could be significantly reduced if $k_2/k'_2$ was well away from unity.

D. Evaluation of Effects of Slight Discrepancy of the Data from the 1T Model on the MRTM $k'_2$ Estimation To evaluate the effects of a slight discrepancy of the data from the 1T model on the MRTM $k'_2$ estimation, another tissue compartment in parallel with the original 1T compartment was added such that the total $V_T$ and $K_1$ were kept constant according to the following equation:

$$C_T(t)=[(1-\alpha)K_1 e^{-k2t}+\alpha\beta K_1 e^{-\beta k2t}] \otimes Cp(t) \quad \text{Equation 3}$$

where $\alpha$ and $\beta$ are constants that determine the degree of deviation of the model from the 1T model.

FIG. 25A shows a perfect 1T TAC ($\alpha$=0 and $\beta$=0, solid line) and a slightly discrepant 1T TAC ($\alpha$=0.01 and $\beta$=5, solid circle) simulated according to Equation 3 using the parameter values for thalamus in Table 2. This magnitude of deviation from an ideal model is commonly seen in neuroimaging data. FIGS. 25B and C show the bias and variability of $k'_2$, respectively, at target region noise of 1.5% in the $k_2/k'_2$ parameter space when $\alpha$=0.01 and $\beta$=5. In contrast to the case with the data simulated by the perfect 1T model (FIG. 24), MRTM $k'_2$ was significantly biased, where the bias increased with increasing values of $\alpha$ and $\beta$ (data not shown). We set $\alpha$=0.01 and $\beta$=5 for further simulations, because the MRTM $k'_2$ bias was then 21%, which was close to the $k'_2$ bias (24%) for the [$^{18}$F]FP-TZTP data. The MRTM $k'_2$ bias for the slightly discrepant 1T data was dependent on both the $k_2/k'_2$ ratio and the magnitude of $k'_2$ (FIG. 25B). The $k'_2$ bias increased asymptotically as $k_2/k'_2$ approached unity (FIG. 25B). Conversely, the $k'_2$ bias decreased as $k_2/k'_2$ became further away from unity. For example, with $k'_2=0.011$, the $k'_2$ bias was 3.5, 21.0 and 320% when $k_2/k'_2$ was 4.0, 1.6 and 1.0, respectively. The $k'_2$ bias also decreased progressively as the $k'_2$ value increased (FIG. 25B). For example, with $k'_2=0.023$, the bias was 1.0, 7.6 and 210% when $k_2/k'_2$ was 4.0, 1.6 and 1.0, respectively. Finally, the MRTM $k'_2$ variability profile in the $k_2/k'_2$ space for the slightly discrepant 1T data (FIG. 25C) was very similar to that for the unperturbed 1T data (FIG. 24B). These simulation analyses thus showed that the slight discrepancies between the [$^{18}$F]FP-TZTP data and the 1T model could cause significantly biased MRTM $k'_2$ estimation and that both the bias and variability of MRTM $k'_2$ estimation could be significantly reduced if $k_2/k'_2$ was well away from unity.

The simulation analysis has shown that a $k'_2$ bias can be introduced by ROI data that slightly disagrees with the 1T model, by adding another parallel tissue compartment. However, this MRTM $k'_2$ bias is a systematic bias with its characteristics dependent on $k'_2$ and $k_2/k'_2$ (FIG. 25B). As is the case with the $k'_2$ estimation variability, this $k'_2$ bias can be significantly reduced if an input tissue region can be selected such that $k_2/k'_2$ is well away from unity.

The simulation analysis of MRTM $k'_2$ estimation in the $k'_2/k'_2$ space suggests that the $k_2/k'_2$ ratio and the magnitude of $k'_2$ are important to accurate $k'_2$ estimation by MRTM. With $k'_2=0.011$ and, for example, $k'_2/k'_2>3$, both the bias and variability of MRTM $k'_2$ estimation would be very small. However, for the [$^{18}$F]FP-TZTP PET data, there are no regions that can give $k'_2/k'_2>3$. Thus, the availability of two tissue regions with $k'_2/k'_2$ well away from unity and high values of $k'_2$ will depend on the tracer and the type of receptor system being imaged.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method of diagnosing diabetes in a patient comprising:
   a. administering to a patient a positron emission tomography (PET)-compatible tracer, which tracer binds to a vesicular monoamine transporter 2 (VMAT2) receptor;
   b. carrying out a PET scan of the patient; and
   c. applying a PANG MAP method comprising a module selected from the group consisting of (i) Module 1, Module 2, and Module 3, and (ii) Module 1 and Module 3, to the PET scan data,
   wherein Module 1 comprises identifying binding potential (BP) positive voxels extracted from the PET data and generating a functionally defined β-cell region of interest (ROI) time activity curve (TAC); Module 2 comprises applying a three-parameter multilinear reference tissue model (MRTM) and a two-parameter multilinear reference tissue model (MRTM2) to the ROI TAC data from Module 1 to identify BP positive voxels; and Module 3 comprises generating a frequency distribution plot from the BP positive voxels identified in Module 1 or 2, calculating a significant binding capacity (SBC), and comparing the SBC of the patient to the SBC of a control individual, and wherein a SBC generated for the patient that is lower than a SBC of a control individual who does not have diabetes is indicative that the patient has diabetes, wherein SBC=Σ (individual voxel BP above predetermined significant value×voxel volume), and wherein the predetermined significant value is a BP value greater than 0.

2. The method according to claim 1, wherein the PANC MAP method comprises carrying out Module 1, Module 2, and Module 3.

3. The method according to claim 1, wherein the PANC MAP method comprises carrying out Module 1 and Module 3.

4. The method according to claim 1, wherein the tracer is a radiolabeled analog of tetrabenazine.

5. The method according to claim 4, wherein the radiolabeled analog of tetrabenazine is dihydrotetrabenazine (DTBZ).

6. The method according to claim 5, wherein the radiolabeled DTBZ is $^{11}$C-DTBZ or $^{18}$F-DTBZ.

7. The method according to claim 1, wherein the diabetes is type-1 diabetes.

* * * * *